US010709157B2

(12) United States Patent
Langan et al.

(10) Patent No.: US 10,709,157 B2
(45) Date of Patent: Jul. 14, 2020

(54) METHODS FOR THE PRODUCTION AND USE OF MYCELIAL LIQUID TISSUE CULTURE

(71) Applicant: Mycotechnology, Inc., Aurora, CO (US)

(72) Inventors: James Patrick Langan, Denver, CO (US); Brooks John Kelly, Denver, CO (US); Huntington Davis, Broomfield, CO (US); Bhupendra Kumar Soni, Denver, CO (US)

(73) Assignee: MycoTechnology, Inc., Aurora, CO (US)

( * ) Notice: Subject to any disclaimer, the term of this patent is extended or adjusted under 35 U.S.C. 154(b) by 0 days.

(21) Appl. No.: 15/438,576

(22) Filed: Feb. 21, 2017

(65) Prior Publication Data

US 2017/0156383 A1    Jun. 8, 2017

Related U.S. Application Data

(63) Continuation-in-part of application No. 15/144,164, filed on May 2, 2016, now Pat. No. 9,572,364, which is a continuation-in-part of application No. 14/836,830, filed on Aug. 26, 2015, now Pat. No. 9,572,363.

(60) Provisional application No. 62/281,546, filed on Jan. 21, 2016, provisional application No. 62/253,567, filed on Nov. 10, 2015, provisional application No. 62/042,071, filed on Aug. 26, 2014.

(51) Int. Cl.
| | |
|---|---|
| *A23L 27/24* | (2016.01) |
| *A61K 36/06* | (2006.01) |
| *A23L 31/00* | (2016.01) |
| *A23L 27/00* | (2016.01) |
| *A23L 27/30* | (2016.01) |
| *A23L 2/52* | (2006.01) |
| *A23J 3/14* | (2006.01) |
| *A23L 33/10* | (2016.01) |

(52) U.S. Cl.
CPC ............ *A23L 27/24* (2016.08); *A23J 3/14* (2013.01); *A23L 2/52* (2013.01); *A23L 27/33* (2016.08); *A23L 27/36* (2016.08); *A23L 27/86* (2016.08); *A23L 27/88* (2016.08); *A23L 31/00* (2016.08); *A23L 33/10* (2016.08); *A61K 36/06* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 1,822,227 A | 9/1931 | Lendrich et al. | |
| 2,451,567 A | 10/1948 | Elmer et al. | |
| 2,693,664 A | 8/1949 | Szuecs | |
| 2,505,811 A | 5/1950 | Szuecs | |
| 2,693,665 A | 11/1954 | Harry | |
| 2,761,246 A | 9/1956 | Szuecs | |
| 2,928,210 A | 3/1960 | Cirillo et al. | |
| 3,086,320 A | 4/1963 | Burdet | |
| 3,701,714 A | 10/1972 | Okada et al. | |
| 3,749,584 A | 7/1973 | Kurtzman et al. | |
| 3,810,997 A | 5/1974 | Chien | |
| 4,071,973 A | 2/1978 | Iizuka et al. | |
| 4,590,160 A | 5/1986 | Nishihashi et al. | |
| 4,891,220 A | 1/1990 | Byron | |
| 4,996,064 A | 2/1991 | Akano et al. | |
| 5,934,012 A | 8/1999 | Holtz et al. | |
| 6,045,834 A | 4/2000 | Howes et al. | |
| 6,277,396 B1 | 8/2001 | Dente | |
| 6,476,003 B1 | 11/2002 | Jordan et al. | |
| 6,490,824 B1 | 12/2002 | Maekawa et al. | |
| 6,558,943 B1 | 5/2003 | Li et al. | |
| 6,569,475 B2 | 5/2003 | Song | |

(Continued)

FOREIGN PATENT DOCUMENTS

| | | |
|---|---|---|
| CN | 101720960 A | 6/2010 |
| CN | 102860541 A | 1/2013 |

(Continued)

OTHER PUBLICATIONS

Diekman "Sweeteners Facts and Fallacies: Learn the Truth Facts and Fallacies: Learn the Truth About the Different Types of Sweeteners to Better Counsel Patients", Today's Dietitian 14(9): p. 42, Sep. 2012 (Year: 2012).*

Beuchat "Indigenous Fermented Foods", in Biotechnology Set, Second Edition (eds H.-J. Rehm and G. Reed), Wiley-VCH Verlag GmbH, Weinheim, Germany, p. 505-559, 2001 (Year: 2001).*

Fang et al. "Development of Cordyceps sinensis Fermentation Broth Wholesome Beverage [J]." Journal of Anhui Agricultural Sciences 8 (2009) USPTO translation (Year: 2009).*

(Continued)

*Primary Examiner* — Emily A Cordas
(74) *Attorney, Agent, or Firm* — Leydig, Voit & Mayer, Ltd.

(57) ABSTRACT

A method enhancing the taste of a food product, which includes the steps of culturing a mycelial liquid tissue culture in a media, collecting a mycelium-free portion of the mycelial liquid tissue culture, e.g., the supernatant fluid of the mycelial liquid tissue culture, and adding the collected supernatant fluid to a food product in an amount sufficient to enhance the food product's taste. The mycelial liquid tissue culture may include *C. sinensis*, and the culture step may be carried out for between about one and sixty days. The food products include non-nutritive sweeteners, alcoholic beverages, teas, coffees, bitter tasting foods such as cranberry, grapefruit, pomegranate, and coconut, as well as dietary supplements, food additives, pharmaceuticals, and nutraceuticals. The present invention also includes compositions of food products in combination with mycelium-free fluids.

9 Claims, No Drawings

(56) References Cited

U.S. PATENT DOCUMENTS

| | | |
|---|---|---|
| 8,486,675 B2 | 7/2013 | Tang |
| 8,529,981 B2 | 9/2013 | Tang |
| 8,535,907 B2 | 9/2013 | Tang |
| 8,623,445 B2 | 1/2014 | Tang |
| 8,685,475 B2 | 4/2014 | Kwack et al. |
| 8,821,955 B2 | 9/2014 | Tang |
| 9,034,402 B2 | 5/2015 | Wong |
| 9,068,171 B2 | 6/2015 | Kelly et al. |
| 9,427,008 B2 | 8/2016 | Kelly et al. |
| 9,480,274 B2 | 11/2016 | Tang |
| 9,572,363 B2 | 2/2017 | Langan et al. |
| 9,572,364 B2 | 2/2017 | Langan et al. |
| 10,010,103 B2 | 7/2018 | Soni et al. |
| 10,231,469 B2 | 3/2019 | Kelly et al. |
| 2002/0082418 A1 | 6/2002 | Ikewaki et al. |
| 2002/0137155 A1 | 9/2002 | Wasser et al. |
| 2003/0208796 A1 | 11/2003 | Song et al. |
| 2004/0009143 A1 | 1/2004 | Golz-Berner et al. |
| 2004/0035047 A1 | 2/2004 | Hwang et al. |
| 2004/0211721 A1 | 10/2004 | Stamets |
| 2005/0180989 A1 | 8/2005 | Matsunaga |
| 2005/0255126 A1 | 11/2005 | Tsubaki et al. |
| 2005/0273875 A1 | 12/2005 | Elias |
| 2006/0014267 A1 | 1/2006 | Cleaver et al. |
| 2006/0134294 A1 | 6/2006 | McKee et al. |
| 2006/0280753 A1 | 12/2006 | McNeary |
| 2007/0160726 A1 | 7/2007 | Fujii |
| 2008/0031892 A1 | 2/2008 | Kristiansen |
| 2008/0057162 A1 | 3/2008 | Brucker et al. |
| 2008/0107783 A1 | 5/2008 | Anijis et al. |
| 2008/0171104 A1 | 7/2008 | Zhu |
| 2008/0193595 A1 | 8/2008 | De Vuyst et al. |
| 2008/0264858 A1 | 9/2008 | Stamets |
| 2008/0274234 A1 | 11/2008 | Miller |
| 2008/0296223 A1 | 12/2008 | Hiromoto |
| 2008/0299645 A1 | 12/2008 | Holliday |
| 2009/0047236 A1 | 2/2009 | Stamets |
| 2009/0047237 A1 | 2/2009 | Stamets |
| 2009/0053363 A1 | 2/2009 | An |
| 2009/0098244 A1 | 4/2009 | Schatzmayr et al. |
| 2009/0104310 A1 | 4/2009 | Nakajima |
| 2009/0130138 A1 | 5/2009 | Stamets |
| 2009/0220645 A1 | 9/2009 | Martinez |
| 2009/0280212 A1 | 11/2009 | Sugimoto et al. |
| 2010/0055241 A1 | 3/2010 | Nakano et al. |
| 2010/0086647 A1 | 4/2010 | Kristiansen |
| 2010/0183765 A1 | 7/2010 | Laan Van Der et al. |
| 2010/0203189 A1 | 8/2010 | Holliday |
| 2010/0203194 A1 | 8/2010 | Salminen et al. |
| 2010/0221385 A1 | 9/2010 | Matsui et al. |
| 2010/0239711 A1 | 9/2010 | Li |
| 2010/0266726 A1 | 10/2010 | Ogura et al. |
| 2010/0316763 A1 | 12/2010 | Choi et al. |
| 2011/0008384 A1 | 2/2011 | Stamets |
| 2011/0052758 A1 | 3/2011 | Greiner-Stoeffele |
| 2011/0070332 A1 | 3/2011 | Bernaert et al. |
| 2011/0081448 A1 | 4/2011 | Dunphy et al. |
| 2011/0091579 A1 | 4/2011 | Hausman |
| 2011/0123675 A1 | 5/2011 | Bernaert et al. |
| 2011/0189220 A1 | 8/2011 | Yang |
| 2011/0200551 A1 | 8/2011 | Stamets |
| 2011/0206721 A1 | 8/2011 | Nair |
| 2011/0229616 A1 | 9/2011 | Anijis et al. |
| 2011/0250339 A1 | 10/2011 | Onishi et al. |
| 2011/0262593 A1 | 10/2011 | Binggeli et al. |
| 2011/0268980 A1 | 11/2011 | Kalisz et al. |
| 2012/0027889 A1 | 2/2012 | Portella |
| 2012/0028345 A1 | 2/2012 | Ibrahim et al. |
| 2012/0034339 A1 | 2/2012 | Giuliani et al. |
| 2012/0034344 A1 | 2/2012 | Menon et al. |
| 2012/0082754 A1 | 4/2012 | Holliday |
| 2012/0100249 A1 | 4/2012 | Laan et al. |
| 2012/0128823 A1 | 5/2012 | Camu |
| 2012/0171308 A1 | 7/2012 | Da Luz Moreira et al. |
| 2012/0177781 A1 | 7/2012 | Hayashi |
| 2012/0190093 A1 | 7/2012 | Fukuda |
| 2012/0231114 A1 | 9/2012 | Bezerrz De Oliveira et al. |
| 2012/0244254 A1 | 9/2012 | Takahashi |
| 2012/0321744 A1 | 12/2012 | Chhun et al. |
| 2013/0209608 A1 | 8/2013 | Berends et al. |
| 2013/0209609 A1 | 8/2013 | Moreno et al. |
| 2013/0337114 A1 | 12/2013 | Binggeli et al. |
| 2014/0065131 A1 | 3/2014 | Kelly et al. |
| 2014/0065263 A1 | 3/2014 | Kelly et al. |
| 2014/0105928 A1 | 4/2014 | Stamets |
| 2014/0170264 A1 | 6/2014 | Kelly et al. |
| 2014/0302560 A1 | 10/2014 | Kelly |
| 2015/0257405 A1 | 9/2015 | Kelly et al. |
| 2015/0257406 A1 | 9/2015 | Kelly et al. |
| 2015/0272155 A1 | 10/2015 | Kelly et al. |
| 2016/0058049 A1 | 3/2016 | Langan et al. |
| 2016/0120201 A9 | 5/2016 | Kelly et al. |
| 2016/0249660 A1 | 9/2016 | Langan et al. |
| 2017/0295837 A1 | 10/2017 | Soni et al. |
| 2018/0064148 A1 | 3/2018 | Langan et al. |
| 2018/0303044 A1 | 10/2018 | Soni et al. |
| 2019/0254305 A1 | 8/2019 | Kelly et al. |
| 2019/0364921 A1 | 12/2019 | Kelly et al. |
| 2020/0060310 A1 | 2/2020 | Schmidt et al. |

FOREIGN PATENT DOCUMENTS

| | | |
|---|---|---|
| DE | 4341316 A1 | 6/1995 |
| EP | 1 173 544 A1 | 1/2002 |
| EP | 0 946 106 B1 | 5/2002 |
| EP | 1 428 440 A1 | 6/2004 |
| EP | 1 695 631 A1 | 8/2006 |
| EP | 2 474 221 A1 | 2/2011 |
| EP | 1 534 088 B1 | 9/2011 |
| EP | 2 591 683 A2 | 5/2013 |
| EP | 2 166 879 B1 | 10/2014 |
| GB | 2059243 A | 4/1981 |
| JP | S50-037742 A | 12/1975 |
| JP | S59-135840 A | 4/1984 |
| JP | S61-219340 A | 8/1986 |
| JP | S62-091161 A | 4/1987 |
| JP | H02-057154 A | 2/1990 |
| JP | H04-126037 A | 12/1999 |
| JP | H11-346657 A | 12/1999 |
| JP | 2003-116342 A | 4/2003 |
| JP | 2005-027540 A | 2/2005 |
| JP | 2005-073508 A | 3/2005 |
| JP | 2006-211987 A | 8/2006 |
| JP | 2011-041540 A | 3/2011 |
| JP | 2011-103901 A | 6/2011 |
| KR | 2002-0027971 A | 4/2002 |
| KR | 10-1487724 B1 | 2/2015 |
| NL | 7322 C | 4/1921 |
| WO | 2001/032830 A2 | 5/2001 |
| WO | 2006/107208 A2 | 10/2006 |
| WO | 2007/031186 A1 | 3/2007 |
| WO | 2010/038867 A1 | 4/2010 |
| WO | 2011/012680 A2 | 2/2011 |
| WO | 2011/032244 A1 | 3/2011 |
| WO | 2011/151831 A1 | 12/2011 |
| WO | WO 2012/104726 A2 | 8/2012 |
| WO | 2013/171194 A1 | 11/2013 |
| WO | 2014/055035 A1 | 4/2014 |
| WO | 2014/145256 A1 | 9/2014 |
| WO | 2014/145265 A2 | 9/2014 |
| WO | 2016/033241 A1 | 3/2016 |
| WO | 2016/138476 A1 | 9/2016 |

OTHER PUBLICATIONS

Jonathan et al. (2011) "Evaluation of Ten Wild Nigerian Mushrooms for Amylase and Cellulase Activities," Mycobiol. 39(2):103-108.

Thammawat et al. (2008) "Isolation, Preliminary Enzyme Characterization and Optimization of Culture Parameters for Production of Naringinase Isolated from Aspergillus niger BCC 25166," Kasetsart J. (Nat. Sci.) 42:61-72.

International Search Report with Written Opinion corresponding to International Patent Application No. PCT/US2017/027731, dated Jul. 19, 2017.

(56) References Cited

OTHER PUBLICATIONS

Willis et al. (2010) "Effect of Dietary Fungus Myceliated Grain on Broiler Performance and Enteric Colonization with Bifidobacteria and *Salmonella*," International Journal of Poultry Science. 9(1):48-52.
Wu et al. (2011) "Ling Zhi-8 mediates p53-dependent growth arrest of lung cancer cells proliferation via the ribosomal protein S7-MDM2-p53 pathway," Carcinogenesis. 32(12):1890-1896.
Yin et al. (2010) "Purification, Characterization and Immuno-Modulating Properties of Polysaccharides Isolated from Flammulina velutipes Mycelium," Am. J. Chin. Med. 38(1):191-204.
Zhang et al. (2004) "Induction of HL-60 apoptosis by ethyl acetate of Cordyceps sinensis fungal mycelium," Life Sciences. 75:2911-2919.
Zhang et al. (2010) "Mycelial growth and polysaccharide content of Polyporus umbellatus," Journal of Medicinal Plants Research. 4(18):1847-1852.
Zhong et al. (2004) "Submerged Cultivation of Medicinal Mushrooms for Production of Valuable Bioactive Metabolites," Adv. Biochem. Eng. Biotechnol. 87:25-59.
Zhou et al. (2009) "Cordyceps fungi: natural products, pharmacological functions and developmental products," Journal of Pharmacy and Pharmacology. 61:279-291.
International Preliminary Report on Patentability corresponding to International Patent Application No. PCT/US2014/029989, dated Sep. 15, 2015.
International Preliminary Report on Patentability corresponding to International Patent Application No. PCT/US2014/029998, dated Sep. 15, 2015.
International Search Report with Written Opinion corresponding to International Patent Application No. PCT/US2014/029989, dated Aug. 12, 2014.
International Search Report with Written Opinion corresponding to International Patent Application No. PCT/US2014/029998, dated Sep. 11, 2014.
International Search Report with Written Opinion corresponding to International Patent Application No. PCT/US2015/047036, dated Jan. 29, 2016.
International Search Report with Written Opinion corresponding to International Patent Application No. PCT/US2016/019929, dated May 19, 2016.
Office Action corresponding to Japanese Patent Application No. 2016-503300, dated Sep. 21, 2016—with English translation.
Office Action corresponding to Japanese Patent Application No. 2016-503304, dated Sep. 30, 2016—with English translation.
Office Action corresponding to U.S. Appl. No. 13/844,685, dated Feb. 19, 2014.
Search Report corresponding to European Patent Application No. 14763975.1, dated Sep. 14, 2016.
Search Report corresponding to European Patent Application No. 14765389.3, dated Nov. 17, 2016.
"Can You Eat Mycelium?" (2014) wiki.answers.com.
"Eat Mycelium cakes?" (2014) Mycotopia.net.
"Eat Mycelium?" (2014) fungifun.com.
"Eating mycelium to trip," (2014) shroomery.org.
"Eating Mycelium" (2014) wisegeek.com Conjecture Corporation.
"Eating Mycelium?" (2014) zoklet.net.
Ali et al. (2010) "Production of pyrazine flavours by mycelial fungi," Master's thesis, University of Pretoria.
Autoclave Search (2014) www.merriam-webster.com/medlineplus/autoclave.
Berovic et al. (2003) "Submerged cultivation of Ganoderma lucidum biomass and immunostimulatory effects of fungal polysaccharides," J. Biotechnol. 103(1):77-86.
Beuchat (2001) "13 Indigenous Fermented Foods," In; Biotechnology. 2nd Ed. Eds: Rehm et al. Wiley-VCH Verlag GmbH. Weinheim, Germany. pp. 505-559.
Bok et al. (1999) "Antitumor sterols from the mycelia of Cordyceps sinensis," Phytochemistry. 51:891-898.

Chang et al. (2002) "Bioactive Polysaccharides from Traditional Chinese Medicine Herbs as Anticancer Adjuvants," The Journal of Alternative and Complementary Medicine. 8(5):559-565.
Chang et al. (2009) "Gandoderma lucidum Extract Promotes Immune Responses in Normal BALB/c Mice In Vivo," In Vivo. 23:755-760.
Crafack et al. (2013) "Influencing cocoa flavour using Pichia Kluyvera and Kluyveromyces marxianus in a defined mixed starter culture for cocoa fermentation," International Journal of Food Microbiology. 167:103-116.
De Melo et al. (2008) "Influence of Flammulina velutipes mycelia culture conditions on antimicrobial metabolite production," Mycoscience. 50(1):78-81.
Diekman (Sep. 2012) "Sweeterners Facts and Fallacies: Learn the Truth about the Different Types of Sweeterners to Better Counsel Patients," Today's Dietitian. 14(9):42-45.
Emden (2015) "Decaffeination 101: Four Ways to Decaffeinate Coffee" Coffee Connection; retrieved from: http://www.coffeeconfidential.org/health/decaffeination/ Jan. 29, 2015. 7 pages.
Encyclopedia Britannica, Louis Pasteur, Datasheet [online]. Copyright 2014 Encyclopedia Britannica Inc. [retrieved on Feb. 6, 2014]. Retrieved from the Internet: <URL: http://www.britannica.com/Ebchecked/topic/445964/Louis-Pasteur>. Specif, p. 3.
Firenzuoli et al. (2008) "The Medicinal Mushroom Agaricus blazei Murrill: Review of Literature and Pharmaco-Toxicological Problems," Evid. Based Complement Alternat. Med. 5(1):3-15.
Foster (2014) "What is Mycelium?" wisegeek.com. Conjecture Corporation.
Han (2005) "Solid-state fermentation of cornmeal with the basidiomycete Ganoderma lucidum for degrading starch and upgrading nutritional value," J. Appl. Micro. 99:910-915.
Hashim (1997) "Effect of Processing on Flavour Precursors, Pyrazines and Flavour Quality of Malaysian Cocoa Beans," PhD thesis, Universiti Pertanian Malaysia.
He et al. (2010) "Patented Techniques for Detoxification of Mycotoxins in Feeds and Food Matrices," Recent Patents on Food, Nutrition & Agriculture. 2:96-104.
Ikrawan (2003) "Influence of Carboxypeptidases on Cocoa Specific Aroma Precursors and Methylpyrazines in Under-Fermented Cocoa Beans," PhD thesis, Universiti Putra Malaysia.
Ishikawa et al. (2001) "Antimicrobial Cuparene-Type Sesquiterpenes, Enokipodins C and D, from a Mycelial Culture of Flammulina velutipes," J. Nat. Prod. 64(7):932-934.
Kamimura (1989) "Removal of Mycotoxins during Food Processing" Tokyo Metropolitan Research Laboratory of Public Health Article. pp. 88-94.
Kang (2003) "Studies on chemical constituents of the mycelia from fermented culture of Flammulina velutipes," Zhongguo Zhong Yao Za Zhi. 28(11):1038-1040.—Abstract Only.
Kang (2005) "Studies on chemical constituents in the mycelia from fermented culture of Flammulina velutipes," Zhongguo Zhong Yao Za Zhi. 30(30):193-195.—Abstract Only.
Konno et al. (2002) "Anticancer and Hypoglycemic Effects of Polysaccharides in edible and Medicinal Maitake Mushroom [*Grifola frondosa*(Dicks.:Fr.) S.F. Gray]," International Journal of Medicinal Mushrooms. 4(3):10-21.
Kuo et al. (1996) "Cordyceps sinensis as an Immunomodulatory Agent" Am. J. Chin. Med. 24:111-125.
Lakshmi et al. (2003) "Antiperoxidative, anti-inflammatory, and antimutagenic activities of ethanol extract of the mycelium of Ganoderma lucidum occurring in South India," Teratog. Carcinog. Mutagen. 1:85-97.—Abstract Only.
Lee et al. (2003) "Biological activities of the polysaccharides produced from submerged culture of the edible Basidiomycete Grifola frondosa," Enzyme and Microbial Technology. 32(5):574-581.
Lefeber et al. (2012) "On-farm implementation of a starter culture for improved cocoa bean fermentation and its influence on the flavour of chocolates produced thereof," Food Microbiology. 30:379-392.
Liu et al. (2012) "Improving the Fermentation Production of the Individual Key Triterpene Ganoderic Acid Me by the Medicinal Fungus Ganoderma lucidum in Submerged Culture," Molecules. 17:12575-12586.

(56) References Cited

OTHER PUBLICATIONS

McMahon (2014) "How Can I Make Tempeh?" wisegeek.com Conjecture Corporation.
MicrobiologyBytes "Introduction to Mycology," Datasheet. Updated Apr. 8, 2009 [retrieved on Feb. 6, 2014]. Retrieved from the Internet: <URL: http://www.microbiologybytes.com/introduction/mycl.html>. Specif, p. 8.
Morris et al. (2003) "Immunomodulating effects of hot-water extract from Pleurotus ostreatus mycelium on cyclophosphamide treated mice," Micologia Aplicada Internacional. 15(1):7-13.—Abstract Only.
Nowrousian et al. (2007) "The novel ER membrane protein PRO41 is essential for sexual development in the filamentous fungus *Sordaria macrospora*," Molecular Microbiology. 64(4):923-937.
Ogundero (1983) "Thermophilic fungi and fermenting cocoa beans in Nigeria," Mycopathologia. 82:159-165.
Pandey et al. (2000) "Use of Various Coffee Industry Residues for the Cultivation of Pleurotus streatus in Solid State Fermentation," Acta Biotechnol. 20(1):41-52.
Paterson (2006) "Ganoderma—a therapeutic fungal biofactory," Phytochemistry. 67:1985-2001.
Schwan (1998) "Cocoa Fermentations Conducted with a Defined Microbial Cocktail Inoculum," Applied and Environmental Microbiology. 64(4):1477-1483.
Schwan (2004) "The Microbiology of Cocoa Fermentation and its Role in Chocolate Quality," Critical Reviews in Food Science and Nutrition. 44:205-221.
Shao et al. (2001) "Determination of nucleosides in natural Cordyceps sinensis and cultured Cordyceps mycelia by capillary electrophoresis," Electrophoresis. 22(1):144-150.
Sone et al. (1985) "Structures and Antitumor Activities of the Polysaccharides Isolated from Fruiting Body and the Growing Culture of Mycelium of Ganoderma lucidum," Agricultural and Biological Chemistry. 49(9):2641-2653.
Stamets (2003) "Culturing Mushroom Mycelium on Agar Media," Ch. 12 In; Growing Gourmet and Medicinal Mushrooms. pp. 89-92.
Taylor (2001) "Measuring Fungal Growth," Chapter 3.8 In; Microorganisms and Biotechnology. 2nd Ed. Thomas Nelson, Ltd. Delta Place, Cheltenham, U. K. (ISBN 0 17 448255 8). Specif. p. 4 (book p. 44).
Tsubouchi et al. (1987) "Effect of roasting on ochratoxin A level in green coffee beans inoculated with Aspergillus ochraceus," Mycopathologia. 97:111-115.
Ulziijargal et al. (2011) "Nutrient Compositions of Culinary-Medicinal Mushroom Fruiting Bodies and Mycelia," Int. J. Med. Mushrooms. 13(4):343-349.
Wasser (2002) "Medicinal mushrooms as a source of antitumor and immunomodulating polysaccharides," Appl. Microbiol. Biotechnol. 60:258-274.
Japanese Patent Office, Notice of Reasons for Rejection in Japanese Patent Application No. 2017-511231 (dated Apr. 16, 2018).
Australian Patent Office, Examination Report No. 1 for Australian Patent Application No. 2015308905 (dated Sep. 20, 2017).
European Patent Office, Extended European Search Report in European Patent Application No. 15836640.1 (dated Dec. 11, 2017).
Korean Patent Office, Office Action in Korean Patent Application No. 10-2017-7008177 (dated May 21, 2018).
Kim et al. (2005), "A comparative study on the production of exopolysaccharides between two entomopathogenic fungi Cordyceps militaris and Cordyceps sinensis in submerged mycelial cultures", J. Applied Microbiology, 99: 728-738.
Schindler et al. (2012) "Improvement of the Aroma of Pea (*Pisum sativum*) Protein Extracts by Lactic Acid Fermentation," Food Biotechnol. 26(1):58-74.
Hadar et al. (1986) "Chemical Composition of the Edible Mushroom Pleurotus ostreatus Produced by Fermentation," Appl. Environ. Microbiol. 51:1352-1354.
Mind Media (Oct. 12, 2006) "Liquid Culture Basics," Shroomery.org. Available on the Internet at URL: https://www.shroomery.org/9145 [Last Accessed Jun. 12, 2017].
Nagai et al. (2006) "Characterization of honey from different floral sources. Its functional properties and effects of honey species on storage of meat," Food Chemistry. 97:256-262.
Namebright "Technique Sheet: Culture Media for Fungi," Available on the Internet at URL: www.centralpamushroomclub.org/sites/default/files/culture.pdf. [Last Accessed Feb. 12, 2015].
Song et al. (2002) "Antioxidant properties of Antrodia camphorata in submerged culture," Journal of Agricultural Food Chemistry 50:3322-3327.
Tang et al. (2002) "Fed-batch fermentation of Ganoderma lucidum for hyperproduction of polysaccharide and ganoderic acid," Enzyme Microbial Technol. 31:20-28.
Japanese Patent Office, Third Office Action issued in JP 2017-511231 dated Aug. 2, 2019.
Chinese First Office Action and Search Report issued in CN 201580045846 dated Jul. 9, 2019.
Fang et al. (2009) "Development of *Cordyceps sinesis* Fermentation Broth Wholesome Beverage" J Anhui Agri Science, 37(8): 3762-3764.
Korean Patent Office, Third Office Action issued in Korean Patent Application No. 10-2017-7008177 dated May 16, 2019.
Japanese Patent Office, Second Office Action issued in JP 2017-511231 dated Nov. 5, 2018.
Korean Patent Office, Second Office Action issued in Korean Patent Application No. 10-2017-7008177 dated Jan. 8, 2019.
List of Designated Additives, the website of The Japan Food Chemical Research Foundation [online], Dec. 10, 1999, [retrieved on Oct. 29, 2018] from the Internet, <URL:https://www.ffcr.or.jp/shokuhin/1999/12/58C1B6DAEF61DFA04925684600097831.html>, Brief explanation of relevance found in Japanese Office Action issued in JP P 2017-511231 dated Nov. 5, 2018.
Brazilian Preliminary Office Action dated Nov. 5, 2019 in BR112017002819-0.
Singapore Supplementary Examination Report (allowance) issued in SB 10201810374W dated Nov. 1, 2019.
India First Examination Report issued in 201737007977 dated Feb. 27, 2020.
Chinese Second Office Action, issued in 201580045846X dated Apr. 17, 2020.
Dando et al., "Adenosine enhances sweet taste through A2B receptors in the taste bud," (2012) J. Neurosci. 32(1):322-330.
Huang et al. (2009) "Determination and analysis of cordycepin and adenosine in the products of *Cordyceps* spp.", Afr. J. Microbiol. Res. 3(12) pp. 957-961.
Leung, P.H. et al., (2006) "Mycelium cultivation, chemical composition and antitumour activity of a *Tolypocladium* sp. fungus isolated from wild Cordyceps sinensis,", Journal of Applied Microbiology 101, pp. 275-283.

* cited by examiner

METHODS FOR THE PRODUCTION AND USE OF MYCELIAL LIQUID TISSUE CULTURE

CROSS-REFERENCE TO RELATED APPLICATIONS

This application is a continuation-in-part of U.S. patent application Ser. No. 15/144,164, filed May 2, 2016, entitled "Methods for the Production and Use of Mycelial Liquid Tissue Culture,", which is in turn a continuation in part of U.S. patent application Ser. No. 14/836,830, filed Aug. 26, 2015, entitled "Methods For The Production And Use Of Mycelial Liquid Tissue Culture", which claims the benefit of U.S. Provisional Application No. 62/042,071, filed Aug. 26, 2014, entitled "Taste Improved Stevia Extract and Tea by Mycotechnological Methods"; this application also claims the benefit of U.S. Provisional Application No. 62/253,567, filed Nov. 10, 2015, entitled "Methods For The Production And Use Of Mycelial Liquid Tissue Culture", and also claims the benefit of U.S. Provisional Application No. 62/281,546, filed Jan. 21, 2016, entitled "Methods For The Production And Use Of Mycelial Liquid Tissue Culture", the disclosure of each of which is hereby incorporated by reference herein in its entirety.

TECHNICAL FIELD

The present invention is directed to the products, and uses thereof, made with mycelial liquid tissue culture of the gourmet and therapeutic higher order Basidiomycetes and Ascomycetes, by the methods of the present invention.

BACKGROUND

U.S. Pat. No. 2,693,665 discusses culturing *Agaricus campestris* in citrus juice, pear juice, asparagus juice, "organic material", a carbohydrate, a nitrogen source and any combination of these materials optionally supplemented with urea and/or various ammonium salts to produce a mycelium for use as a foodstuff.

U.S. Pat. No. 2,761,246 discloses a method for the production of submerged *Morchella esculenta* and Helvellaceae spp. mycelium for human food. This document discusses the use of various molasses solutions as media with ammonium salt supplements. The patent discloses that added calcium carbonate or calcium sulfate acts as hyphal sphere nucleation sites, increasing biomass yield 30 fold.

U.S. Pat. No. 2,928,210 discloses a method to produce mushroom mycelium from sulfite liquor waste media supplemented with organic and inorganic salts.

U.S. Pat. No. 3,086,320 discloses a method to improve the flavor of submerged mycelium of *Morchella esculenta, Helvella gigas, Coprinus comatus,* and *Agaricus campestris*, by growing the strains in a media that "must contain, in water, a carbohydrate as a source of energy, a source of nitrogen and suitable minerals", and includes recipes comprising milk, which is claimed to improve yield and flavor of mycelium when used properly.

U.S. Pat. No. 4,071,973 discusses culturing conditions for Basidiomycetes. Fungus is inoculated and grown in inorganic nutrient salts for nitrogen, phosphate and potassium, mixed with sucrose at 50-70 g/L and supplemented with fine powder of "crushed sugarcane, sugarcane bagasse, pine tree-tissue and wheat bran" at 0.2-15 g/L. Oxygen is controlled at 30-90% (v/v) to the media, the vessel pressurized at 0.12-0.5 MPa (17.4-72.5 psi) with oxygen supplied at 0.1-1.0 L/minute. Salts used include ammonium nitrate, sodium phosphate, magnesium sulfate heptahydrate, iron (II) sulfate heptahydrate and dipotassium hydrogen phosphate. Creative air pressure cycles are discussed and controlled with a pressure regulator. An alternative engineering scheme would use a back-pressure regulator, with a pressure regulator on the air receiver tank supplying the air.

Organizations around the world have been diligently looking for novel bitter blockers. Only a handful of patents on bitter blockers have been filed, and many are on synthetic compounds or rely on permutations of a basis molecular motif, see, e.g., EP2570035A1, U.S. Pat. Nos. 4,154,862, 5,631,292, 6,265,012, 7,939,671, US20080226788A1, US20100227039A1, US20020177576, US20110086138 and WO2008119197A1.

Stevia (*Stevia rebaudiana*) has been used by human societies for thousands of years as a folk medicine and sweetener. Today many countries grow the plant, including Korea, Taiwan, Thailand, Malaysia, Brazil, Colombia, Peru, Paraguay, Uruguay, and Israel. The FDA labeled both rebaudioside A and stevioside as Generally Recognized As Safe (GRAS), resulting in a number of stevia extract food additives entering the United States market. The term "stevia" is generally used to refer to the leaves and/or plant parts, either fresh or dried, or an extract/decoction/syrup of *Stevia rebaudiana* leaf, either crude or further purified to specific glycosides, the term "stevia" as used henceforth used in this document can refer to any of these forms of the plant. The compounds responsible for the sweet taste and metallic and bitter aftertaste of *S. rebaudiana* are known as the steviol glycosides. 10 have been identified in total, and the class of compounds is marked by various glycosylated, rhamnosylated, and xylated forms of the aglycone diterpene steviol.

To produce steviol glycosides, stevia plants are dried and subjected to an extraction process. The various glycosides can be obtained in different purities via crystallization with various solvents such as methanol or ethanol, by column chromatography, or filtration.

Various methods have been employed to alter the taste profile of green tea. Fermented teas have been consumed for hundreds of years, though this has always been conducted with environmental flora. Teas are fermented typically no shorter than three months, and sometimes as long as 50 years.

What is desired is a way of manufacturing a food product, such as, for example, stevia or tea that achieves a good tasting product while reducing the taste defects. Thus, a need remains in the art for products having reduced levels of undesirable taste components and/or increased levels of flavor and/or health promoting components relative to stevia or tea, and for methods of obtaining such products. The present invention is directed toward overcoming one or more of the problems discussed above.

SUMMARY OF THE INVENTION

In one embodiment, the present invention includes a method for enhancing the taste of a food product, which can include the steps of culturing a mycelial liquid tissue culture in a media, collecting the supernatant fluid of the mycelial liquid tissue culture; and adding the collected supernatant fluid to a food product in an amount sufficient to enhance the food product's taste.

The fungus used to culture the mycelial tissue can include at least one of the following species: *Ganoderma lucidum, Ganoderma applanatum, Cordyceps sinensis, Cordyceps militaris, Hericium erinaceus, Lentinula edodes, Agaricus* blazei, *Grifola frondosa, Auricularia auricula, Flammulina velutipes, Trametes versicolor, Morchella* spp., *Inonotus obliquus, Laricifomes officinalis, Fomes fomentarius, Fomes officinalis, Fomes fomitopisis, Tricholoma matsutake, Boletus edulis, Clitocybe nuda, Clitocybe saeva, Plearotus* spp., *Tremella fuciformis, Piptoporus betulinis, Polyporus umbellatus, Pholiota nameko, Volvariella volvacea, Hypsizygus marmoreus, Stropharia rugosoannulata,* and *Laetiporus sulfureus*. In one embodiment, the fungus is *Cordyceps sinensis*.

In some embodiments, the food product's taste is enhanced when combined with the collected supernatant fluid. The taste enhancements may take any form, such as, for example, reducing bitter tastes, reducing undesirable aftertastes, and reducing astringency in the food product.

The food product can include food ingredients, dietary supplements, food additives, nutraceuticals, and pharmaceuticals. An example of a food product includes *stevia* rebaudioside A, steviol glycoside, *stevia* plant parts, whole wheat, coffee, tea, amaranth, *quinoa*, pea protein, monk fruit, aspartame, acesulfame-k, beer, liquor, spirits, wine, sucralose, carbohydrates, potassium chloride, cacao, cacao liquor, ginseng, sugar alcohol, cranberry, grapefruit, pomegranate, and coconut.

In one embodiment, the collected supernatant fluid can be optionally pasteurized or sterilized. The collected supernatant fluid can also be optionally dried, either before or after the optional pasteurization or sterilization step.

In some embodiments, the culturing step can be carried out for between about one and about sixty days.

The present invention also includes compositions which comprise a combination of a food product and a mycelium-free portion from a mycelial liquid tissue culture. In some embodiments, prior to combination, the mycelium-free portion from the mycelial liquid tissue culture is a dried supernatant and the food product is a dried food product.

Various modifications and additions can be made to the embodiments discussed without departing from the scope of the invention. For example, while the embodiments described above refer to particular features, the scope of this invention also included embodiments having different combination of features and embodiments that do not include all of the above described features.

DETAILED DESCRIPTION OF THE INVENTION

While various aspects and features of certain embodiments have been summarized above, the following detailed description illustrates a few embodiments in further detail to enable one of skill in the art to practice such embodiments. The described examples are provided for illustrative purposes and are not intended to limit the scope of the invention.

In the following description, for the purposes of explanation, numerous specific details are set forth in order to provide a thorough understanding of the described embodiments. It will be apparent to one skilled in the art, however, that other embodiments of the present invention may be practiced without some of these specific details. Several embodiments are described and claimed herein, and while various features are ascribed to different embodiments, it should be appreciated that the features described with respect to one embodiment may be incorporated with other embodiments as well. By the same token, however, no single feature or features of any described or claimed embodiment should be considered essential to every embodiment of the invention, as other embodiments of the invention may omit such features.

Unless otherwise indicated, all numbers used herein to express quantities, dimensions, and so forth used should be understood as being modified in all instances by the term "about." In this application, the use of the singular includes the plural unless specifically stated otherwise, and use of the terms "and" and "or" means "and/or" unless otherwise indicated. Moreover, the use of the term "including," as well as other forms, such as "includes" and "included," should be considered non-exclusive. Also, terms such as "element" or "component" encompass both elements and components comprising one unit and elements and components that comprise more than one unit, unless specifically stated otherwise.

In one embodiment, the present invention is based on the discovery that fungi cultured media (on any media as described herein) such as *Cordyceps sinensis, Hericum erinaceus,* or *Ganoderma lucidum* cultured media, can be used directly as a foodstuff, after suitable treatment such as pasteurization or sterilization prior to consumption. The cultured media can be dried, diluted, concentrated, or used neat in the forms of a concentrate, dried powder, and the like.

As a stationary mycelial mat cultures, the interface between fungal metabolite solution and remaining media steadily sinks. Interface displacement is a convenient observation for determining the health of the culture, and indicates when the culture has entered a stationary or growth phase. The forming metabolite pool often has a pleasant coloration and without being bound by theory, is believed to contain beneficial fungal material such as enzymes, carbohydrates, lipids, small molecules, and so forth that would make the material desirable as a food ingredient/supplement/additive. The inventors have found that the mycelial culture, in one embodiment, need only be filtered (with, e.g., cheesecloth, coffee filter, 0.2 micron filter) and pasteurized to isolate the supernatant fluid. Floating cultures can be used according to the present invention if blended.

In one embodiment, the present inventors have found that the a portion of a fungal liquid tissue culture fluid, the supernatant fluid (containing reduced amounts of mycelium, herein referred to as the "mycelium-free portion") when added directly to a food product, has the ability to improve undesirable tastes in the food product, such as, for example, bitter tastes, astringent tastes, and/or undesirable aftertastes. Enhancing the taste of a food product includes improved sweetening by that food product. Flavor improvement also includes reduction of characteristic aftertastes associated with *stevia* and tea, including, without limitation, a bitter flavor, a metallic flavor, a licorice flavor, commonly as an aftertaste, which sets on after the initial sweet or tea sensation. The bitter blocker is also capable of eliminating metallic tastes in products such as potassium chloride. The bitter blocker can also be used to reduce undesirable flavor defects in breads and formulations made from various grains such as *quinoa*, amaranth and whole wheat. Reducing these tastes may also be referred to as mitigating taste defects. For example, steviol glycosides possess residual bitterness and aftertaste, which affect its qualitative characteristics.

Improved flavor of food products treated by products of the invention may be measured in a variety of ways, such as the chemical analysis which demonstrate improved sweetness, reduced bitterness and/or mitigated taste defects. Taste tests with taste panels may also be conducted to provide qualitative data with respect to improved taste(s) in the products, with the panels determining whether improved sweetness and/or decreased taste defects have been exhibited in the treated products.

Accordingly, the present invention relates to compositions comprising combinations of a mycelium-free portion of a mycelial liquid tissue culture with food products, as well as methods by which to improve a food product's taste by adding a mycelium-free portion of a mycelial liquid tissue culture to the food product wherein the combination of the food product and the mycelium-free portion of a mycelial liquid tissue culture has an enhanced taste. The compositions comprising the combinations have enhanced tastes relative to the food product alone. In one embodiment, the present invention includes myceliating *Stevia rebaudianna* leaves with, for example, *Cordyceps sinensis* to provide a better tasting *S. rebaudianna* aqueous extract compared to the unmyceliated control. However, the present inventors also found that simply adding a whole liquid culture of *C. sinensis* to a sample of *S. rebaudianna* aqueous extract eliminated undesirable aftertastes of the *S. rebaudianna* (e.g., an unpleasant aftertaste). For example, a 60% Rebaudioside A mixture was incubated with a whole liquid tissue culture of *C. sinensis* and *G. lucidum*. The inventors found that the commonly associated aftertaste of the steviol glycoside mixture was completely eliminated when mixed with the whole liquid culture of *Cordyceps sinensis* after a 6 hour incubation. Conditions for the same effects by other fungal species, *G. lucidum, Hericium erinaceus, Grifola frondosa, Lentinula edodes, Tricholoma* matsutake, *Morchella esculenta, Trametes versicolor* or *Ganoderma lucidum* were not identified. However, it is understood by the inventors that the property of improving taste profile will likely be found in other genii of fungus, and likely other species of *Cordyceps* fungus, such as, for example, any species of *Ophiocordyceps, Elaphocordyceps*, or *Cordyceps*, such as *C. sinensis* and *C. militaris*.

Specifically, the inventors used filtered *C. sinensis* liquid tissue culture to mix with a steviol glycoside mixture for six hour incubation. After running a time course study, the inventors surprisingly discovered that the flavor enhancing effect took hold immediately upon the addition of the filtrate to the steviol glycoside mixture, indicating that the process was possibly non-enzymatic. It was conjectured that the filtered *C. sinensis* liquid tissue culture (also known as the mycelium-free portion of a mycelial liquid tissue culture) had taste improving and/or bitter blocker properties. The filtered *C. sinensis* liquid tissue culture (filtrate) was then combined with other substances as disclosed herein, for example, in Table 9 and found to have general taste improving/bitter blocker properties for these substances. The inventors found that the filtrate may be further purified, for example, to increase solubility, and may be dried, such as spray-drying, and combined with food products to improve the food products' taste profiles, including reducing bitter tastes and/or aftertastes. The present invention thus discloses a bitter blocker that appears to be effective in a number of different types of food products.

In one embodiment, the present invention includes a method for enhancing the taste of a food product, which includes the steps of culturing a mycelial liquid tissue culture in a media, collecting a mycelium-free portion of the culture, and adding the mycelium-free portion to a food product to enhance the food products' taste.

A food product according to the present invention can include any food product, which includes any substances which are taken by oral administration (by mouth), and includes food products, food ingredients, non-caloric sweeteners, salt substitutes, dietary supplements, food additives, pharmaceuticals, foodstuffs, cosmetic ingredients, nutraceutical ingredients, dietary ingredients, and processing aids. Any food product which has or can have undesirable taste characteristics, such as bitter tastes, undesirable aftertastes, astringent tastes, and the like, can be treated with the bitter blocker composition of the present invention. In some embodiments, the food product includes tea plant parts, tea decoctions, or tea purified extracts. In some embodiments, the food product includes *stevia* rebaudioside A, steviol glycoside, *stevia* plant parts, whole wheat, coffee, tea, amaranth, *quinoa*, pea protein, monk fruit, aspartame, acesulfame-k, beer, liquor, spirits, wine, sucralose, carbohydrates, potassium chloride, cacao, cacao liquor, ginseng, sugar alcohol, cranberry, grapefruit, pomegranate, and coconut.

Food products include all cereals, grains, all species of wheat, rye, brown rice, white rice, red rice, gold rice, wild rice, rice, barley, triticale, rice, sorghum, oats, millets, *quinoa*, buckwheat, fonio, amaranth, teff and durum; apples and pears, apricots, cherries, almonds, peaches, strawberries, raisins, manioc, cacao, banana, Rubiaceae sp. (coffee), lemons, oranges and grapefruit; tomatoes, potatoes, peppers, eggplant, Allspice, mango powder, *Angelica*, Anise (*Pimpinella anisum*), Aniseed myrtle (*Syzygium anisatum*), Annatto (*Bixa orellana*), Apple mint (*Mentha suaveolens*), *Artemisia vulgaris*, Mugwort, Asafoetida (*Ferula assafoetida*), *Berberis*, Banana, Basil (*Ocimum basilicum*), Bay leaves, Bistort (*Persicaria bistorta*), Black cardamom, Black cumin, Blackcurrant, Black limes, Bladder wrack (*Fucus vesiculosus*), Blue Cohosh, Blue-leaved Mallee (*Eucalyptus polybractea*), Bog Labrador Tea (*Rhododendron groenlandicum*), Boldo (*Peumus boldus*), Bolivian Coriander (*Porophyllum ruderale*), Borage (*Borago officinalis*), *Calamus, Calendula*, Calumba (*Jateorhiza calumba*), Chamomile, *Cannabis*, Caper (*Capparis spinosa*), Caraway, Cardamom, Carob Pod, *Cassia, Casuarina*, Catnip, Cat's Claw, Catsear, Cayenne pepper, *Celastrus paniculatus*, Comfrey, Celery salt, Celery seed, Centaury, Chervil (*Anthriscus cerefolium*), Chickweed, Chicory, Chile pepper, Chili powder, Cinchona, Chives (*Allium schoenoprasum*), Cicely (*Myrrhis odorata*), Cilantro (see Coriander) (*Coriandrum sativum*), Cinnamon (and *Cassia*), Cinnamon Myrtle (*Backhousia myrtifolia*), Clary, Cleavers, Clover, Cloves, Coffee, Coltsfoot, Comfrey, Common Rue, Condurango, Coptis, Coriander, Costmary (*Tanacetum balsamita*), Couchgrass, Cow Parsley (*Anthriscus sylvestris*), Cowslip, Cramp Bark (*Viburnum opulus*), Cress, Cuban Oregano (*Plectranthus amboinicus*), Cudweed, Cumin, Curry leaf (*Murraya koenigii*), Damiana (*Turnera aphrodisiaca*), Dandelion (*Taraxacum officinale*), Demulcent, Devil's claw (*Harpagophytum procumbens*), Dill seed, Dill (*Anethum graveolens*), Dorrigo Pepper (*Tasmannia stipitata*), Echinacea, Echinopanax Elatum, Edelweiss, Elderberry, Elderflower, Elecampane, *Eleutherococcus senticosus*, Epazote (*Chenopodium ambrosioides*), Ephedra, *Eryngium foetidum, Eucalyptus*, Fennel (*Foeniculum vulgare*), Fenugreek, Feverfew, Figwort, Five-spice powder (Chinese), Fo-ti-tieng, Fumitory, Galangal, Garam masala, Garden cress, Garlic chives, Garlic, Ginger (*Zingiber officinale*), Ginkgo biloba, Ginseng, Ginseng, Siberian (*Eleutherococcus senticosus*), Goat's Rue (*Galega officinalis*), Goada masala, Golden Rod, Golden Seal, Gotu Kola, Grains of paradise (*Aframomum melegueta*), Grains of Selim (*Xylopia aethiopica*), Grape seed extract, Green tea, Ground Ivy, Guaco, Gypsywort, Hawthorn (*Crataegus sanguinea*), Hawthorne Tree, Hemp, Herbes de Provence, Hibiscus, Holly, Holy Thistle, Hops, Horehound, Horseradish, Horsetail (*Equise-*

*tum telmateia*), Hyssop (*Hyssopus officinalis*), Jalap, Jasmine, Jasmin pearl, Jiaogulan (*Gynostemma pentaphyllum*), Joe Pye weed (Gravelroot), John the Conqueror, Juniper, Kaffir Lime Leaves (*Citrus hystrix, C. papedia*), Kaala masala, Knotweed, Kokam, Labrador tea, Lady's Bedstraw, Lady's Mantle, Land cress, Lavender (*Lavandula* spp.), Ledum, Lemon Balm (*Melissa officinalis*), Lemon basil, Lemongrass (*Cymbopogon citratus, C. flexuosus*, and other species), Lemon Ironbark (*Eucalyptus staigeriana*), Lemon mint, Lemon Myrtle (*Backhousia citriodora*), Lemon Thyme, Lemon *verbena* (*Lippia citriodora*), Licorice—adaptogen, Lime Flower, *Limnophila aromatica*, Linseed, Liquorice, Long pepper, Lovage (*Levisticum officinale*), Luohanguo, Mace, Mahlab, Malabathrum, Manchurian Thorn Tree (*Aralia manchurica*), Mandrake, Marjoram (*Origanum majorana*), *Marrubium vulgare*, Marsh Labrador Tea, Marshmallow, Mastic, Meadowsweet, Mei Yen, Melegueta pepper (*Aframomum melegueta*), Mint, Milk thistle (*Silybum*), Bergamot (*Monarda didyma*), Motherwort, Mountain Skullcap, Mullein (*Verbascum thapsus*), Mustard, Mustard seed, *Nashia inaguensis*, Neem, *Nepeta*, Nettle, *Nigella sativa*, Kolanji, Black caraway, Noni, Nutmeg, Mace, Marijuana, *Oenothera* (*Oenothera biennis*), *Olida* (*Eucalyptus olida*), Oregano (*Origanum vulgare, O. heracleoticum*), Orris root, Osmorhiza, Olive Leaf (used in tea and as herbal supplement), *Panax quinquefolius*, Pandan leaf, Paprika, Parsley (*Petroselinum crispum*), Passion Flower, Patchouli, Pennyroyal, Pepper (black, white, and green), Peppermint, Peppermint Gum (*Eucalyptus dives*), *Perilla*, Plantain, Pomegranate, *Ponch phoran*, Poppy seed, Primrose (*Primula*), candied flowers, dry tea mixes, *Psyllium*, Purslane, Quassia, Quatre epices, Ramsons, Raspberry, Raspberry (leaves), Reishi, Restharrow, *Rhodiola rosea*, Riberry (*Syzygium luehmannii*), Rocket/Arugula, Roman chamomile, Rooibos, Rosehips, Rosemary (*Rosmarinus officinalis*), Rowan Berries, Rue, Safflower, Saffron, Sage (*Salvia officinalis*), Saigon Cinnamon, St John's Wort, Salad Burnet (*Sanguisorba minor* or *Poterium sanguisorba*), *Salvia*, Sichuan Pepper (Sansho), *Sassafras*, Savory (*Satureja hortensis, S. montana*), Schisandra (*Schisandra chinensis*), *Scutellaria costaricana*, Senna (herb), *Senna obtusifolia*, Sesame seed, Sheep Sorrel, Shepherd's Purse, Sialagogue, Siberian ginseng (*Eleutherococcus senticosus*), *Siraitia grosvenorii* (luohanguo), Skullcap, Sloe Berries, Smudge Stick, *Sonchus*, Sorrel (*Rumex* spp.), Southernwood, Spearmint, Speedwell, Squill, Star anise, *Stevia*, Strawberry Leaves, Suma (*Pfaffia paniculata*), Sumac, Summer savory, *Sutherlandia frutescens*, Sweet grass, Sweet cicely (*Myrrhis odorata*), Sweet woodruff, Szechuan pepper (*Xanthoxylum piperitum*), Tacamahac, Tamarind, Tandoori masala, Tansy, Tarragon (*Artemisia dracunculus*), Tea, *Teucrium polium*, Thai basil, Thistle, Thyme, Toor Dall, Tormentil, *Tribulus terrestris*, Tulsi (*Ocimum tenuiflorum*), Turmeric (*Curcuma longa*), Uva Ursi also known as Bearberry, Vanilla (*Vanilla planifolia*), Vasaka, Vervain, Vetiver, Vietnamese Coriander (*Persicaria odorata*), Wasabi (*Wasabia japonica*), Watercress, Wattleseed, Wild ginger, Wild Lettuce, Wild thyme, Winter savory, Witch Hazel, Wolfberry, Wood Avens, Wood Betony, Woodruff, Wormwood, Yarrow, Yerba Buena, Yerbe mate, Yohimbe, Za'atar, Zedoary Root, or derivations thereof in aqueous or semi-aqueous solution(s).

The step of culturing a mycelial liquid tissue culture may be accomplished by any methods known in the art. In one embodiment, the methods to cultivate a mycelial liquid tissue culture may be found in, e.g., PCT/US14/29989, filed Mar. 15, 2014, PCT/US14/29998, filed Mar. 15, 2014, U.S. 61/953,821, filed Mar. 15, 2014, U.S. 61/953,823, filed Mar. 15, 2014, U.S. 62/042,071, filed Aug. 26, 2014, all of which are incorporated by reference herein in their entireties.

In one embodiment, the mycelial liquid tissue culture is carried out in a bioreactor pressure vessel which is ideally constructed with a torispherical dome, cylindrical body, and spherical cap base, jacketed about the body, equipped with a magnetic drive mixer, and ports through curled-in jacket spaces to provide access for equipment comprising DO probes, pH meters, conductivity meters, thermocouples, etc., as is known in the art. These meters and probes should be data-logged. In one embodiment, the cylindrical base has a valve connected to a harvesting line which is teed off to a valve to another tee, which is teed-off to a floor sink and in-line with a CIP skid, the harvesting line tee in-line to a pasteurization skid, and finally a drying device, such as a spray dryer, fluid bed dryer, conical dryer, or other drying applications. In one embodiment, the processed mycelial liquid tissue culture can be packaged immediately from the dryer. A sample should be kept as control and an appropriate sample sent to a third-party quality control, Certificate of Analysis provider. Air can be provided by an air receiver tank connected to a 120/240 V air compressor. The air compressor releases air through a pressure regulator with upstream and downstream valves, immediately upstream of the upstream valve being a tee, teed-off to a valve leading to another tee, teed-off to a valve to a CIP skid, in-line with a valved steam supply, the post pressure regulator valve in-line to a valve and 0.2 µm stainless steel filter (which can be cleaned in a sonicating sink) in a stainless steel cartridge housing, which leads to an optional check valve to obligate valve on the dome of the pressure vessel, the final valve system optionally being upstream of the check valve, teed off to a y-piece which leads to two similar check valve to valve setups to 360° sprayballs. The two sprayballs are placed to account for the shadow presented by the air percolator that extends through the vessel. Pressure gauges along the set-up may be strategically placed to monitor pressure, and flow meters used to monitor air supply rates. Additional gas receiver tanks, such as oxygen tanks, can be placed in-line between the pressure regulator and the filters to calibrate partial pressures of any gas. The inventors recommend back to back filter cartridges, though this is not necessary. The gas is exhausted through a check valve with low-cracking pressure, such as a gate-valve, or a spring check valve with 2 to 3 psi cracking pressure, to a back-pressure regulator that holds the vessel at 5 to 25 psi. The back-pressure regulator can also lead to a steam trap and floor-sink. In one embodiment the set-up provides 0.5 to 5.0 ACH. Other engineering schemes known to those skilled in the art may also be used.

The reactor preferably is outfitted with a means for sterile inoculation. In one embodiment, to inoculate the reactor, a glycerol stock solution of fungi, consisting of a valved autoclavable (e.g. polypropylene) container, is taken out of the freezer, removed from its seal and attached to a cross, in-line with a valve to the chamber. The cross cross-line is valved on both ends, with the upstream valve connected to a stainless steel cartridge housing holding a stainless steel 0.2 µm filter. This line is connected to a valved tee (also valved on the upstream side) in-line to the main air supply line. Downstream of the cross is a valve to a steam strap to a floor-sink. The steam is run to sterilize the air between the glycerol stock and the valve to the chamber. Once sterilized and cooled, the vacuum between the glycerol stock and the valve to the chamber is broken. The valves on either side of the cross are closed, and the valves on the glycerol stock and pressure vessel are opened to inoculate the media. Other engineering schemes known to those skilled in the art may also be used.

The reactor should be outfitted to be filled with water. The water supply system is ideally a WFI system, with a sterilizable line between the still and the reactor. Solid media ingredients should be added to the tank pre-sterilization, ideally through a vacuum conveyor system. High temperature sterilizations are fast enough to be not detrimental to the media. Once the water is added, the tank should be mildly agitated and inoculated. In another embodiment, solid media ingredients are added to filtered or distilled water and the liquid media is sterilized at high temperatures and pumped through a sterile line into the pressure vessel. In another embodiment, the tank is filled with filtered or distilled water, the solid media ingredients are added, and the media is sterilized by steaming the either the jacket, chamber, or both, while the media is optionally being agitated.

At least one scale-up reactor should be used before approaching tanks with volumes on the order of $1 \times 10^5$. As many as 3 to 4 are recommended. The inventors recommend going from the order of $1 \times 10^0$ L to $1 \times 10^2$ L to $1 \times 10^4$ L to $1 \times 10^{5-6}$ L. Richer media can be used for the scale-up reactors and pre-glycerol stock culturing motifs.

The glycerol stock disclosed herein is prepared, in one embodiment, by a simple propagation motif of Petri plate to 0.1 L to 4 L Erlenmeyer shake flask to 50% glycerol stock. Petri plates can comprise agar in 25 to 35 g/L in addition to variations of the media described above for bioreactor motif. Conducted in sterile operation, chosen Petri plates growing anywhere from 3 to 90 days can be propagated into 4 L Erlenmeyer flasks (or 250 to 1,000 mL Wheaton jars) for incubation on a shaker table. The smaller the container, the faster the shaker should be. The inventors recommend anywhere from 40 to 160 RPM depending on container size, with about a 1" swing radius. After shaking for 1 to 10 days, an aliquot (e.g. 10 to 500 mL) of the shake flask can be poured into a sterile, valved autoclavable container, which is then adjusted with sterile, room temperature glycerol to 40 to 60% (v/v). The glycerol stocks can be sealed with a water tight seal and can be placed into a sterile plastic bag, sealed, and placed into the freezer at −20° C. for storage and eventual cold shipping to any manufacturing site. The freezer is ideally a constant temperature freezer. Liquid tissue culture stocks not adjusted to glycerol may also be used and stored at 4° C. or −20° F. Glycerol stocks stored at 4° C. may also be used.

The present invention makes use of the concept that any human grade media, excluding any human grade ingredients discussed in the background, can be used as a media recipe for the production of edible liquid mycelial culture, as is known in the art and also disclosed elsewhere, e.g., PCT/US14/29989, filed Mar. 15, 2014, PCT/US14/29998, filed Mar. 15, 2014, U.S. 61/953,821, filed Mar. 15, 2014, U.S. 61/953,823, filed Mar. 15, 2014, U.S. 62/042,071, filed Aug. 26, 2014, all of which are incorporated by reference herein in their entireties. Preferably, a nitrogen salt, if used, is ammonium acetate, as it is the most 'natural' salt. Other supplemental media ingredients include brown rice syrup, molasses, fruit purees (mango, apple, etc.) in concentrations on the order of $1 \times 10^{-2}$ to $1 \times 10^2$ mL/L (or simply as the media), short grain brown rice flour, nutritional yeast flakes, carboxymethyl cellulose, carboxymethyl cellulose salts, whey, casein, and plant and seed protein. Ingredients are chosen so as to minimize possibilities for allergic reactions and provide high yield. Ammonium acetate is optionally incorporated as a batch fed ingredient.

The present invention may also be used with animal-grade media and animal grade food products.

In one embodiment, minimal media liquid tissue cultures are supplemented with large volumes of maximal media, so as to take advantage of short log times and secondary metabolism.

In one embodiment, a fungus strain useful for the fungal component of the present invention in one embodiment is *C. sinensis* strain WC859, commercially available from Pennsylvania State University (The Pennsylvania State University Mushroom Culture Collection, available from the College of Agriculture Sciences, Department of Plant Pathology and Environmental Microbiology, 117 Buckhout Laboratory, The Pennsylvania State University, University Park, Pa., USA 16802). Fungal components useful in the present invention may be prepared by methods described herein. Other methods known in the art may be used.

Alternatively, the fungal liquid tissue culture can include other species of fungi from genus *Cordyceps*, *Ophiocordyceps*, *Elaphocordyceps*, *Metacordyceps*, such as, for example, *C. militaris*. Many other species exist in the genus, however, these species are generally not cultivated commercially. However, it is expected that, for example, *C. scarabaeicola*, *C. takaomontana*, *Ophiocordyceps dipterigena*, *Ophiocordyceps amazonica*, *C. cylindrica*, *Cordyceps sphecocephala*, *Metacordyceps martialis*, *Ophiocordyceps melonlonthae*, *Ophiocordyceps nutans*, *Ophiocordyceps curculionium*, *Ophiocordyceps australis*, *Ophiocordyceps tiputini*, *Cordyceps caloceroides*, and *Cordyceps variabilis* will have the same or similar bitter blocking ability as *C. sinensis*.

Alternatively, fungi suitable for the present invention comprises: *Ganoderma lucidum*, *Ganoderma applanatum*, *C. militaris*, *Hericium erinaceus*, *Lentinula edodes*, *Agaricus blazei*, *Grifola frondosa*, *Auricularia auricula*, *Flammulina velutipes*, *Trametes versicolor*, *Morchella* spp., *Inonotus obliquus*, *Laricifomes officinalis*, *Fomes fomentarius*, *Fomes officinalis*, *Fomes fomitopisis*, *Tricholoma matsutake*, *Boletus edulis*, *Clitocybe nuda*, *Clitocybe saeva*, *Plearotus* spp., *Tremella fuciformis*, *Piptoporus betulinis*, *Polyporus umbellatus*, *Pholiota nameko*, *Volvariella volvacea*, *Hypsizygus marmoreus*, *Stropharia rugosoannulata*, *Laetiporus sulfureus*, and combinations thereof.

In one embodiment, the invention includes a method for preparing a mycelium-free portion of the mycelial liquid tissue culture after culturing. The mycelium-free portion includes mycelial biomolecular supernatant solids, cellular material and residual media of the mycelial liquid tissue culture.

As disclosed hereinabove, to prepare the culture, the prepared media is inoculated into a container of sterilized human grade media in water preferably filtered through any method known in the art, such as reverse osmosis, deionization or distillation. In another embodiment the water is not filtered. In another embodiment the media is animal grade. As disclosed, the flask and media can be sterilized by any method known in the art, such as in situ exposure to 250° F. at 23 PSI saturated steam for an appropriate amount of time, such as 2-2.5 hr for a 4.0 L Erlenmeyer flask filled with 1.5 L of media. The sterilized flask can be inoculated once cool by any means known in the art, such as by a Petri plate, floating or submerged liquid culture, myceliated agricultural material, glycerol stock, etc. The flask is ready for use after 3-60 days of appropriate culturing as is known in the art, such as on a shaker table at 130 RPM at room temperature in a cleanroom. A control Petri plate of the residual culture left in the flask can be made to ensure the flask is void of contamination. The flask can also be used to scale into a larger bioreactor (e.g. 5-500 L) made of the same quality media, which can be used in similar manner.

In some embodiments, the fungal liquid tissue culture is *C. sinensis* grown in a liquid media consisting of 8 g/L organic potato starch powder and 0.8 g/L organic carrot powder. This minimal medium has been found by the inventors to be an effective media recipe for producing the bitter blocker (taste enhancement food product) as previously described. The bitter blocking effect/taste enhancement of the product of the invention can be lost with different media, such as the addition of 20 g/L organic mango puree, which introduces flavor defects in an aqueous steviol glycoside solution. The resulting supernatant powder may be used as a bitter blocker in product applications as discussed herein.

After a suitable time for culturing, which can be determined by one of skill in the art, the mycelium-free portion (as defined herein) can be collected from the culture. This mycelium-free portion of the liquid mycelial liquid tissue culture may optionally be used to improve and/or enhance the taste of a food product. Culturing can take place, for example, for between about one and about sixty days, between about two and about fifty days, between about three and about forty days, between about four and about thirty days, between about five and about twenty-five days, between about six and about twenty days, between about seven and about fifteen days, between about eight and about twelve days, and between about nine and about ten days. The length of time for culturing can be determined by, for example, economic considerations for number of days in culture and the degree of taste enhancement observed for a particular culture time.

The culture to use in the present invention may be any liquid tissue culture comprising mycelium, for example, submerged or floating culture. A submerged culture is generally agitated, whereas the floating culture is minimally agitated, which allows the mycelia to grow in a mat-like form. The portions of the culture to use with the present invention includes any and all parts or portions of the culture, including mycelium, culture supernatant or filtrate, or any proportions or fractions thereof. In one embodiment, the culture may be blended (mechanically or otherwise) prior to use, and the entire blended material used, or some fraction thereof. In some embodiments, the portion of the culture to use is the portion of the culture which is commonly understood as the "cell culture supernatant" or "cell culture filtrate", i.e., the fluid portion of the culture which has been separated from the mycelial cells, and contains a relatively smaller or lesser amount of mycelium as opposed to a mycelial cell portion, which is enriched in mycelial cells, but will still contain some fluid portion. Thus, it should be understood that this fluid tissue culture supernatant will also commonly contain mycelia, even if not visible to the eye or even easily visible under a microscope. This portion of the culture is called herein the "mycelial-free" portion for convenience, however, as stated it should be understood that this portion will commonly contain some minimal amount of mycelia, even if not visible to the eye.

In order to prepare the mycelium-free portion of the culture, the mycelium can be removed by any method known in the art to separate cell culture supernatant fluids. For example, the culture may be filtered by any means known in the art to obtain the filtrate, such as, for example, 0.2 μm filters and the like. Alternatively, the mycelium-free portion of the culture may be collected by centrifugation. The collected mycelium-free portion of the cultured mycelial liquid tissue culture may be referred to herein as collected supernatant, supernatant, supernatant fluid, *C. sinensis* supernatant, filtrate, product, and similar terms such as the taste-enhancing product or bitter blocker/blocking product, or bitter blocker.

Optionally, the liquid tissue culture can be treated to reduce or eliminate the viability of live organisms, such as pasteurization or sterilization, by methods known in the art. The collected liquid tissue culture may be pasteurized or sterilized either before or after separation to obtain the mycelium-free portion of the culture, by any method known in the art. In one embodiment the material is sterilized under conditions such as approximately 30 to 50 minute exposure to 250° F. saturated steam at 23 psi. Alternatively, the material can be pasteurized by holding the material in a hot water bath at 160 to 170° F. for 20 minutes, twice, cooling it back to room temperature in between runs.

This pasteurized or sterilized liquid tissue culture could be used as a novel beverage, or its powder as a novel foodstuff, food ingredient, dietary supplement, dietary ingredient or food additive which can be used from 0.1-40,000 ppm in various product applications.

The filtrate (collected supernatant) e.g., mycelium-free portion of a mycelial liquid tissue culture may have its volume or liquid component adjusted as determined by one of skill in the art to produce concentrates, diluates, or dried powders. In one embodiment, the filtrate may be optionally dried by any method known in the art, including the use of open air drying, small batch desiccators, vacuform dryers, fluid beds or spray dryers, or freeze-driers to dry the liquid to a powder. The filtrate is, in one embodiment, dried following sterilization/pasteurization.

The resulting powder or taste enhancement product may be used to enhance the taste of a food product, and may be mixed into any food/beverage as described herein at concentrations of 0.1-40,000 ppm and even higher depending on the nature of the application Determination of the amount of the taste enhancement product to use may be determined by one of skill in the art by trial with the goal to reduce or eliminate undesirable taste component in the food product and/or enhance the food product's taste, without introducing flavor defects.

A general range of concentrations of *C. sinensis* supernatant (bitter blocker) as a dried powder to use with various food products is shown in Table 9 below. It is within the skill in the art to determine optimum ratios of the *C. sinensis* supernatant to use with a particular product, based on taste profiles. For example, at too high concentrations of *C. sinensis* supernatant, the flavor enhancing effect will cease to be or the product will introduce flavor defects into the final material. At too low of a concentration of supernatant, there will be an insufficient degree of taste improvement. The concentration of the agricultural material, such as a steviol glycoside mixture which is typically used at 200-450 ppm, ultimately determines the ideal bitter blocker concentration. For example, serial dilution/concentration can be used as a tool in determining the upper and lower threshold concentrations use of the supernatant. Formulate the bitter blocker into the material at whatever initial desired concentration one wants to test. If it provides the desired flavor change, halve the concentration until the flavor change is insufficient. Take the final concentrations between what worked and what did not, and apply the bitter blocker at the average. If it works, halve the concentration until it no longer works, and the concentration above the one that doesn't work is the lower threshold concentration. If it doesn't work, double the concentration until it does. The lower threshold concentration can be doubled indefinitely to reach the upper threshold concentration, wherein the taster determines whether the flavor modifying effect is eventually lost or the bitter blocker starts to introduce a flavor defect.

The powder may also be rehydrated, filtered and re-dried to increase solubility of the product. The spray dried product has high solubility and optionally is not rehydrated before use, and may be simply mixed in as a powder with a food product (particularly in non-nutritive sweetener applications). Alternatively, the taste enhancement food product may be combined with a food product in liquid form, and optionally the food product/taste enhancement product may be dried together. The supernatant powder may also be dried in a fluid bed, or spray dried onto a fluidized product and even agglomerated, such as in the production of a steviol glycoside mixture comprising the product.

The present invention includes a bitter blocker product made by the methods disclosed herein.

The present invention offers an effective means of culturing mycelium around the world as human food by means of presenting the inoculant source at a production site in the form of a liquid tissue stock adjusted to 50% (v/v) glycerol, which can be maintained at −20° C. This culture, at least for both strains tested (*G. lucidum* and *C. sinensis*), display the phenomenon of increasing in vigor upon revival the longer it is kept in −20° C. storage, and does not need to be warmed up before propagation.

The present invention also provides for a method to produce a food product, comprising culturing a mycelial liquid tissue culture in a media, collecting the mycelium-free portion of the supernatant, and using the mycelium-free portion of the culture as the food product. Appropriate fungi to use, appropriate media, appropriate methods of collecting the mycelium free portion of the supernatant are disclosed herein. The mycelium-free portion of the culture fluid (or conditioned media) can be used on its own as a food product. The mycelium free portion may be optionally concentrated, diluted or dried as disclosed herein, and may be combined with any food product as disclosed herein prior to use. The present invention also includes combination products comprising one or more food product(s) and mycelium-free portion made from a mycelial liquid tissue culture made by the processes disclosed herein.

Therefore, in another embodiment, provided is a composition comprising a combination of one or more food products of the invention, and a mycelium-free portion from a mycelial liquid tissue culture. In one embodiment, the mycelial liquid tissue culture is produced by methods of the present invention.

In one embodiment, the mycelium-free portion from a mycelial liquid tissue culture is a dried or partially dried filtrate or supernatant from the mycelial liquid tissue culture. The composition may include the mycelium-free portion of a mycelial liquid tissue culture obtained from a fungus as previously defined herein, and may include, for example, *Cordyceps sinensis*, and/or *Cordyceps militaris*.

The mycelium free portion of the mycelial liquid tissue culture may be obtained by any methods known in the art, including methods disclosed herein. Such methods include the steps of culturing a mycelial liquid tissue culture in a media, separating the mycelium-free fluid from the mycelial cells, and collecting the mycelium-free fluid as the mycelium-free portion of the mycelial liquid tissue culture.

The composition, in some embodiments, has a taste enhancement which includes reduced bitter tastes, reduced undesirable aftertastes, reduced metallic tastes, and/or reduced astringency compared to the food product alone.

Compositions may be formed from food products that are dried prior to combination with the mycelium-free portion of a mycelial liquid tissue culture. In some embodiments, prior to combination with a food product, the mycelium-free portion of a mycelial liquid tissue culture is dried. Thus, a dried food product may be combined with a dried mycelium-free portion of a mycelial liquid tissue culture to form the composition.

Food products that may be included in compositions of the invention include food products according to the invention, and include, for example, non-nutritive sweeteners and nutritive sweeteners. These include, without limitation, non-nutritive sweeteners such as mogroside, mogroside mixtures, aspartame, acesulfame-k, sucralose, steviol glycoside mixtures, *stevia* plant parts, and combinations thereof. Another category of food products includes, for example, whole wheat, coffee, tea, amaranth, *quinoa*, pea protein, monk fruit, monk fruit extract, beer, liquor, spirits, wine, sucralose, carbohydrates, potassium chloride, cacao, cacao liquor, ginseng, sugar alcohol, cranberry, grapefruit, pomegranate, and coconut.

Food products may also include coffee, roasted coffee beans, roasted coffee grinds, tea leaves, or brewed tea. Also, food products include protein concentrates, e.g., a product comprising greater than 50% protein. Such a food product can be obtained from a number of sources, including vegetarian sources as well as non-vegetarian sources. Vegetarian sources include protein concentrates and isolates prepared from a vegetarian source such as pea, rice, soy, hemp, and other sources, or a combination thereof. Typically a protein concentrate is made by removing the oil and most of the soluble sugars from a meal made of the starting material, such as soybean meal. A protein concentrate may still contain a significant portion of non protein material, such as fiber. Typically, protein concentrations in a concentrate are between 65-90%. A protein isolate typically removes most of the non-protein material such as fiber and may contain up to about 90% protein. A protein isolate is typically dried and is available in powdered form and may alternatively called "protein powder."

Vegetarian sources of protein have some advantages over non-vegetarian sources of protein. Whey or casein protein isolates will also contain some amount of lactose and can cause difficulties for those who are lactose-intolerant. Egg protein isolates may cause problems in those who are allergic to eggs and are also quite expensive. Soy protein isolates contain all of the essential amino acids and is inexpensive. Rice protein is easily digestible but is deficient in some amino acids and therefore does not provide a "complete" protein. Hemp protein is a complete protein, and pea protein, while containing all essential amino acids, does not contain them in the correct ratios.

The food product may also be obtained from non-vegetarian sources, such as egg, whey, casein, beef, and/or combinations thereof. Alternatively, the methods of the invention can be used with concentrated protein powders made from pea, rice, soy, hemp, whey, casein, egg and the like, and hydrolyzed forms of same and combinations thereof.

A food product may also include products taken by mouth, such as dietary supplements, vitamins, food additives, pharmaceuticals, and nutraceuticals. Many of these types of products have unpleasant tastes, including caffeine and polyphenols, calcium, vitamins, cough syrups, probiotics, and the like. Vitamins include vitamin A, vitamin D, vitamin E (e.g., d-alpha-tocopherol, d-alpha-tocopheryl acetate, dl-alpha-tocopherol and dl-alpha-tocopheryl acetate), vitamin B1 and derivatives thereof, vitamin B2 and derivatives thereof, vitamin B6 and derivatives thereof (e.g., pyridoxine hydrochloride), vitamin C and derivatives thereof (e.g., ascorbic acid, sodium L-ascorbate, etc.), vitamin B12 and derivatives thereof, fluoride (e.g., sodium fluoride), calcium, magnesium, iron, proteins, amino acids, amino saccharides (amino sugars), oligosaccharides, and combinations thereof.

Pharmaceuticals may include drugs or quasi-drugs that are administered orally or used in the oral cavity (e.g., vitamins, cough syrups, cough drops, chewable medicine tablets, amino acids, bitter-tasting agents, acidulants or the like), wherein the drug may be in solid, liquid, gel, or gas form such as a pill, tablet, spray, capsule, syrup, drop, troche agent, powder, and the like; personal care products such as other oral compositions used in the oral cavity such as mouth freshening agents, gargling agents, mouth rinsing agents, toothpaste, tooth polish, dentrifices, mouth sprays, teeth-whitening agent and the like; dietary supplements; animal feed; nutraceutical products, which includes any food or part of a food that may provide medicinal or health benefits, including the prevention and treatment of disease (e.g., cardiovascular disease and high cholesterol, diabetes, osteoporosis, inflammation, or autoimmune disorders), non-limiting, examples of nutraceuticals include naturally nutrient-rich or medicinally active food, such as garlic, soybeans, antioxidants, fibers, phytosterols and phytostanols and their esters, glucosamine, chondroitin sulfate, stenol, stanol, ginseng, ginko, *echinacea*, or the like; other nutrients that provide health benefits, such as amino acids, vitamins, minerals, carotenoids, dietary fiber, fatty acids such as omega-3 or omega-6 fatty acids, DHA, EPA, or ALA which can be derived from plant or animal sources (e.g., salmon and other cold-water fish or algae), flavonoids, phenols, polyols, polyphenols (e.g., catechins, proanthocyanidins, procyanidins, anthocyanins, quercetin, resveratrol, isoflavones, curcumin, punicalagin, ellagitannin, citrus flavonoids such as hesperidin and naringin, and chlorogenic acid), prebiotics/probiotics, phytoestrogens, sulfides/thiols, policosanol, saponin, rubisco peptide, appetite suppressants, hydration agents, autoimmune agents, C-reactive protein reducing agents, or anti-inflammatory agents; or any other functional ingredient that is beneficial to the treatment of specific diseases or conditions, such as diabetes, osteoporosis, inflammation, or high cholesterol levels in the blood.

The following examples are provided for illustrative purposes only and are not intended to limit the scope of the invention.

EXAMPLES

Example 1

An RO filtered aqueous extract was made from 1 lb. of organic/fresh potato and carrot, and 1 L of organic fruit juice to create 1 L cultures in 6, 4 L Erlenmeyer flasks. These cultures were made with anywhere from 0-100% *stevia*/tea aqueous extract. The flasks were autoclaved and cooled. Once cool, a log phase Petri plate culture of *C. sinensis* WC859 was propagated into the flask and subsequently agitated (60 RPM with a ½ inch swing radius). A fully developed liquid tissue culture (growing in log phase) was observed in about 3-4 days. 20 g of *stevia* leaf was placed in a food-grade container and about 100 mL of log phase liquid culture as described above was added to the container. The container was allowed to incubate, covered, at about 75 degrees F. for about six hours. After incubation the *stevia* leaves were lightly pasteurized and dried. 5 g of the treated *stevia* leaves were soaked in one cup of water, filtered and tasted in a randomized double-blind test with untreated *stevia* by five testers. The testers found that the treated *stevia* had increased sweetness compared to untreated control *stevia* and had a mitigated bitter/licorice aftertaste.

Example 2

An RO filtered aqueous extract was made from 1 lb. of organic/fresh potato and carrot, and 1 L of organic fruit juice to create 6, 1 L cultures in 4 L Erlenmeyer flasks. These cultures were made with 0-100% aqueous tea extract. The flasks were autoclaved and cooled. Once cool, a log phase Petri plate culture of *C. sinensis* strain WC859 was propagated into the flask and subsequently agitated (60 RPM with a ½ inch swing radius). A fully colonized log-phase liquid tissue culture was observed in about 3-4 days. Approximately 20 g of green tea leaves were placed in a food-grade container and about 100 mL of log phase culture as described above was added to the container. The container was allowed to incubate, covered, at about 75 degrees F. for about six hours. After the incubation was finished, according to taste testing, the green tea leaves were lightly rinsed, mildly pasteurized, and dried. 5 g of the treated green tea leaves were dried and brewed in one cup of water, filtered and tasted in a randomized, double-blind test with untreated control green tea leaves by five testers. The testers found that the treated green tea leaves had decreased bitterness compared to the control green tea leaves.

Example 3

A clean, 1.5 L handled glass bottle was filled with 1 L of media consisting of 17 g/L agar, 8 g/L organic potato starch, 0.8 g/L organic carrot powder, and 20 mL/L organic mango puree. The lid of the handled glass bottle was loosely screwed on and covered with tin foil. The inventors recommend the use of these handled glass bottles due to their handles, which make pouring easier. The bottle was placed in an autoclave and sterilized on a 2.33 hour liquid cycle. Once the cycle was complete, the bottle was quickly placed in a laminar sterile flow hood to cool until it could be touched, which took about 1.3 hours. At this point, the contents of the bottle were carefully poured into 120 Petri plates. The plates cooled overnight in the hoods.

Once cool, fungi from stock cultures were used to inoculate the recently poured plates. These fungi were growing on an identical media. The fungi were transferred with sterile 12" bamboo skewers which had been autoclaved in a mason ball jar with the agar from the previous day. One of these species of fungus was *Hericium erinaceus*. 15 *H. erinaceus* plates were made and one was selected for propagation into a 4 L Erlenmeyer flask 8 days after propagation. On the $7^{th}$ day of growth, the 4 L Erlenmeyer flask was prepared. The flask contained 1.5 L of media, consisting of 8 g/L corn flour, 4 g/L organic oat flour, 2 g/L organic mango puree and 2 g/L organic potato starch powder. The flask shook at 60 RPM for 6 days on a 1" swing radius. On the $2^{nd}$ day of this culture, a 100 L bioreactor was filled with 58 L of RO water, and a concentrate containing 800 g organic potato starch powder, 80 g organic carrot powder, 50 g blended organic soft white wheat berries and 1 L organic mango puree, adjusted to 2 L with RO water, was poured into the reactor to bring the volume to 60 L. The reactor was not jacketed so 121 to 122° C. was injected and vented into the chamber through manifolds connected to the pressure vessel head set up by one of skill in art. The bioreactor was sterilized on a 4.5 hour liquid cycle, and filled to 85 L due to steam condensation. The reactor cooled to room temperature for four days through thermal diffusion, at which point it was inoculated.

The vessel had access to an air-inlet line, which comprised a ¼ horsepower, 115 V, 50/60 Hz air compressor supplying air through two in-inline 0.2 µm autoclavable capsule filters, through a check-valve and ball-valve into the chamber. The entire capsule filter valve set-up was sterilized before sterilizing the bioreactor and media, and assembled onto the bioreactor in sterile operation. Once cool after 86 hours, air was run to pressurize the vessel, but instead of running through an air exhaust manifold, the air exhaust manifold was closed and a pressure gauge on the head of the vessel immediately removed so as to create a positively pressured nozzle. The lid of the submerged *H. erinaceus* culture was removed, the top 5 inches of the Erlenmeyer flask flamed down with a propane torch by one of skill in the art, and, once the flask is cool (an 8 second wait time), the flask was poured into the bioreactor through the positively pressured nozzle. The pressure gauge was placed back onto the reactor, and the air exhaust manifold immediately opened. The reactor pressure equilibrated at 2-3 psi, the cracking pressure of the entry and exit check-valves. Petri plates of the *H. erinaceus* inoculant were made for QC.

Air was supplied as such, and the bioreactor cultured for 13 days. The culture appeared to enter log phase on day 2, and grew vibrantly with 0.5 cm spheres until day 9, where cell division appeared to stop. On the $13^{th}$ day, the contents of the bioreactor were poured into a 6 $m^2$ plastic tub with 10 inch walls with lips, the tub being coated with food-grade plastic sheeting. The tub was kept at a height of about 4 feet, and two fans were positioned to blow air over the tub. After four days, the culture had dried, and a beef jerky like material was recovered and blended to yield 724 g of powder. The powder had a very light carrot taste, and primarily a cereal-esque taste that was very neutral.

Example 4

A 4 L flask filled with 1.5 L of 8 g/L organic potato starch and 0.8 g/L organic carrot powder in RO water was sterilized and inoculated from a two week old P1 *C. sinensis* culture. After culturing for 7 days at room temperature at 60 RPM (1" swing radius), the culture was filtered through three stacked coffee filters, pasteurized for 40 minutes at 165° F. and placed in a small batch desiccator at 140° F. overnight. The following day the dried material was collected and blended with a yield of 4.5 g/L for a total of 6.75 g. 5 g of the harvested material was poured into 1 L of RO water and shaken intermittently for 15 minutes. From this stock culture, 53.34 mL of solution was added to another solution containing 1 kg of 97% rebaudioside A dissolved in 1.6 L of RO water. This solution was thoroughly mixed and dried in a small batch desiccator overnight, and the resulting material was blended and packaged in a clean ziplock bag, having a concentration of the collected filtrate solids of 2,667 ppm. 150 mg of this mixture was added to 500 mL of RO water to create a solution of 300 ppm 97% rebaudioside A to 0.8 ppm *C. sinensis* supernatant solids. When taste tested against a control, it was obvious to all three inventors that the aftertaste of the steviol glycoside mixture containing the *C. sinensis* supernatant solids was undetectable compared to a control 300 ppm 97% rebaudioside A solution.

Example 5

A 4 L flask filled with 1.5 L of 8 g/L organic potato starch and 0.8 g/L organic carrot powder in RO water was sterilized and inoculated from a two week old P1 *C. sinensis* culture. After culturing for 15 days at room temperature at 60 RPM (1" swing radius), the culture was filtered through three stacked coffee filters, pasteurized for 40 minutes at 165° F. and placed in a small batch desiccator at 140° F. overnight. The following day the dried material was collected and blended with a yield of 4.1 g/L for a total of 6.15 g. 5 g of the harvested material was poured into 1 L of RO water and shaken intermittently for 15 minutes. From this stock culture, 53.34 mL of solution was added to another solution containing 1 kg of 97% rebaudioside A dissolved in 1.6 L of RO water. This solution was thoroughly mixed and dried in a small batch desiccator overnight, and the resulting material was blended and packaged in a clean ziplock bag, having a concentration of the collected filtrate solids of 2,667 ppm. 150 mg of this mixture was added to 500 mL of RO water to create a solution of 300 ppm 97% rebaudioside A to 0.8 ppm *C. sinensis* supernatant solids. When taste tested against a control, it was obvious to all three inventors that the aftertaste of the steviol glycoside mixture containing the *C. sinensis* supernatant solids was undetectable compared to a control 300 ppm 97% rebaudioside A solution.

Example 6

A 4 L flask filled with 1.5 L of 8 g/L organic potato starch and 0.8 g/L organic carrot powder in RO water was sterilized and inoculated from a two week old P1 *C. sinensis* culture. After culturing for 35 days at room temperature at 60 RPM (1" swing radius), the culture was filtered through three stacked coffee filters, pasteurized for 50 minutes at 165° F. and placed in a small batch desiccator at 140° F. overnight. The following day the dried material was collected and blended with a yield of 5.5 g/L for a total of 8.25 g. 5 g of the harvested material was poured into 1 L of RO water and shaken intermittently and heated on a hot plate turned to medium for 15 minutes. From this stock culture, 53.34 mL of solution was added to another solution containing 1 kg of 97% rebaudioside A dissolved in 1.6 L of RO water. This solution was thoroughly mixed and dried in a small batch desiccator overnight, and the resulting material was blended and packaged in a clean ziplock bag, having a concentration of the collected filtrate solids of 2,667 ppm. 150 mg of this mixture was added to 500 mL of RO water to create a solution of 300 ppm 97% rebaudioside A to 0.8 ppm *C. sinensis* supernatant solids. When tasted against a control, it was obvious to all three inventors that the aftertaste of the steviol glycoside mixture containing the *C. sinensis* supernatant solids was undetectable compared to a control 300 ppm 97% rebaudioside A solution.

Example 7

A 4 L flask filled with 1.5 L of 8 g/L organic potato starch and 0.8 g/L organic carrot powder in RO water was sterilized and inoculated from a two week old P1 *C. sinensis* culture. After culturing for 7 days at room temperature at 60 RPM (1" swing radius), the culture was filtered through cheesecloth, pasteurized for 50 minutes at 160° F. and placed in a small batch desiccator at 130° F. overnight. The following day the dried material was collected and blended with a yield of 4.4 g/L for a total of 6.6 g. 5 g of the harvested material was poured into 1 L of RO water and shaken intermittently for 15 minutes. From this stock culture, 53.34 mL of solution was added to another solution containing 1 kg of 97% rebaudioside A dissolved in 1.6 L of RO water. This solution was thoroughly mixed and dried in a small batch desiccator overnight, and the resulting material was blended and packaged in a clean ziplock bag, having a concentration of the collected filtrate solids of 2,667 ppm. 150 mg of this mixture was added to 500 mL of RO water to create a solution of 300 ppm 97% rebaudioside A to 0.8 ppm *C. sinensis* supernatant solids. When taste tested against a control, it was obvious to all three inventors that the aftertaste of the steviol glycoside mixture containing the *C. sinensis* supernatant solids was undetectable compared to a control 300 ppm 97% rebaudioside A solution.

Example 8

A 4 L flask filled with 1.5 L of 8 g/L organic potato starch and 0.8 g/L organic carrot powder in RO water was sterilized and inoculated from a two week old P1 *C. sinensis* culture. After culturing for 10 days at room temperature at 60 RPM (1" swing radius), the culture was filtered through three stacked coffee filters, pasteurized for 40 minutes at 170° F. and placed in a small batch desiccator at 140° F. overnight. The following day the dried material was collected and blended with a yield of 4.6 g/L for a total of 6.9 g. 5 g of the harvested material was poured into 1 L of RO water and shaken intermittently for 15 minutes. From this stock culture, 40.00 mL of solution was added to another 1.6 L solution of distilled water containing 1 kg of 97% rebaudioside A. This solution was thoroughly mixed and dried in a small batch desiccator overnight, and the resulting material was blended and packaged in a clean ziplock bag, having a concentration of the collected filtrate solids of 2,000 ppm. 150 mg of this mixture was added to 500 mL of RO water to create a solution of 300 ppm 97% rebaudioside A to 0.6 ppm *C. sinensis* supernatant solids. When taste tested against a control, it was obvious to all three inventors that the aftertaste of the steviol glycoside mixture containing the *C. sinensis* supernatant solids was undetectable compared to a control 300 ppm 97% rebaudioside A solution. This steviol glycoside mixture tasted very similar to the mixture containing 0.8 ppm supernatant solids.

Example 9

A 4 L flask filled with 1.5 L of 8 g/L organic potato starch and 0.8 g/L organic carrot powder in RO water was sterilized and inoculated from a 10 day old P1 *C. sinensis* culture. After culturing for 4 days at room temperature at 60 RPM (1" swing radius), the culture was filtered through cheesecloth and placed in a small batch desiccator at 140° F. overnight. The following day the dried material was collected and blended with a yield of 4.5 g/L for a total of 6.75 g. 5 g of the harvested material was poured into 1 L of RO water and shaken intermittently for 15 minutes. From this stock culture, 53.34 mL of solution was added to another solution containing 1 kg of 97% rebaudioside A dissolved in 1.6 L of RO water. This solution was thoroughly mixed and dried in a small batch desiccator overnight, and the resulting material was blended and packaged in a clean ziplock bag, having a concentration of the collected filtrate solids of 2,667 ppm. 150 mg of this mixture was added to 500 mL of RO water to create a solution of 300 ppm 97% rebaudioside A to 0.8 ppm *C. sinensis* supernatant solids. When taste tested against a control, it was obvious to all three inventors that the aftertaste of the steviol glycoside mixture containing the *C. sinensis* supernatant solids was undetectable compared to a control 300 ppm 97% rebaudioside A solution.

Example 10

A 4 L flask filled with 1.5 L of 8 g/L organic potato starch and 0.8 g/L organic carrot powder in RO water was sterilized and inoculated from a two week old P1 *C. sinensis* culture. After culturing for 7 days at room temperature at 60 RPM (1" swing radius), the culture was filtered through three stacked coffee filter and placed in a small batch desiccator at 140° F. overnight. The following day the dried material was collected and blended with a yield of 4.5 g/L for a total of 6.75 g. 5 g of the harvested material was poured into 1 L of RO water and shaken intermittently for 15 minutes. From this stock culture, 53.34 mL of solution was added to another solution containing 1 kg of 60% rebaudioside A dissolved in 1.6 L of RO water. This solution was thoroughly mixed and dried in a small batch desiccator overnight, and the resulting material was blended and packaged in a clean ziplock bag, having a concentration of the collected filtrate solids of 2,667 ppm. 150 mg of this mixture was added to 500 mL of RO water to create a solution of 300 ppm 60% rebaudioside A to 0.8 ppm *C. sinensis* supernatant solids. When taste tested against a control, it was obvious to all three inventors that the aftertaste of the steviol glycoside mixture containing the *C. sinensis* supernatant solids was undetectable compared to a control 300 ppm 60% rebaudioside A solution.

Example 11

A 4 L flask filled with 1.5 L of 8 g/L organic potato starch and 0.8 g/L organic carrot powder in RO water was sterilized and inoculated from a 20 day old P1 *C. sinensis* culture. After culturing for 7 days at room temperature at 60 RPM (1" swing radius), the culture was filtered through a 0.2 μm vacuum filter and placed in a small batch desiccator at 150° F. overnight. The following day the dried material was collected and blended with a yield of 4.3 g/L for a total of 6.45 g. 5 g of the harvested material was poured into 1 L of RO water and shaken intermittently for 15 minutes. From this stock culture, 53.34 mL of solution was added to another solution containing 1 kg of 60% rebaudioside A dissolved in 1.6 L of RO water. This solution was thoroughly mixed and dried in a small batch desiccator overnight, and the resulting material was blended and packaged in a clean ziplock bag, having a concentration of the collected filtrate solids of 2,667 ppm. 150 mg of this mixture was added to 500 mL of RO water to create a solution of 300 ppm 60% rebaudioside A to 0.8 ppm *C. sinensis* supernatant solids. When taste tested against a control, it was obvious to all three inventors that the aftertaste of the steviol glycoside mixture containing the *C. sinensis* supernatant solids was undetectable compared to a control 300 ppm 60% rebaudioside A solution.

Example 12

16 different media recipes to determine the effect of media on bitter blocking activity against a sample of 60% rebaudioside A using the method of Example 4, while varying media as shown below. Table 1 below shows what media were tested and the sensory response summaries.

TABLE 1

Effect of Media on Bitter Blocking Activity against 60% rebaudioside A*

| Media Recipe | Result |
|---|---|
| Nutritional Yeast | No stevia aftertaste, though introduced a new undesirable aftertaste |
| Brown Rice Syrup | No aftertaste, typical up front flavor, no new flavors introduced |
| Corn & Oat Flours | No aftertaste, very nice up front stevia flavor no new flavors introduced |
| Potato Starch Powder | No aftertaste, typical up front stevia flavor, no new flavors introduced |
| Barley Flour | No aftertaste, duller up front stevia flavor, no new flavors introduced |
| Kelp | No aftertaste, muted up front stevia flavor, no new flavors introduced |
| Green Tea | No aftertaste, introduces a tea flavor defect up front |
| Carrot Powder | No aftertaste, nice up front stevia flavor, no new flavors introduced |
| Brown Rice Flour | No aftertaste, nice up front stevia flavor, no new flavors introduced |
| Blackstrap Molasses | No aftertaste, mild up front stevia flavor, no new flavors introduced |
| Sodium Carboxymethylcellulose | No aftertaste, mild up front stevia flavor, no new flavors introduced |
| Wheat Flour | No aftertaste, dull up front stevia flavor, no new flavors introduced |
| Rye Flour | No aftertaste, dull up front stevia flavor, no new flavors introduced |
| Oat Flour | No aftertaste, dull up front stevia flavor, no new flavors introduced |
| Corn Flour | No aftertaste, mild up front stevia flavor, no new flavors introduced |

*All media made with 8 g/L of material, the corn/oat sample being made with 5 g/L and 3 g/L respectively.
Product was tasted at 300 ppm 60% reb A and 0.8 ppm supernatant powder.

Table 1 shows that many recipes are applicable to the production of the bitter blocker though not every recipe works. The inventors recommend the potato/carrot or corn/oat recipe as described herein.

Example 13

The molecular composition of the disclosed bitter blocker was determined from a sample made from two 40 L batches of a 200 L *C. sinensis* submerged culture grown in an 8 g/L organic potato starch powder and 0.8 g/L organic carrot powder RO water media. The culture had been harvested at 41 and 48 days for a total of 230 g of powder bitter blocker (a yield of ~2.9 g/L), which was mixed together. 150 g of the sample was used for third party compositional analysis. The data, taken in technical duplicate, shows that this batch of bitter blocker is 86.9% carbohydrate. The material is further composed of, in descending rank of concentration: water, ash, fat and protein. No molecules foreign to the food supply were detected in this study. These data are summarized in Table 2, while more detailed information is shown in subsequent tables. Kilocalories (commonly called 'calories' on food labels) are listed as well. The bitter blocker is typically processed on the $8^{th}$-$12^{th}$ day of culturing, but this approach was taken to develop understanding of the most concentrated form of the product, i.e. the most transformed media.

TABLE 2

Summary of biological components in the bitter blocker*

|  | Run 1 | Run 2 | Average |
|---|---|---|---|
| Moisture (Vacuum oven) | 6.0 | 6.0 | 6.0 |
| Protein | 1.0 | 1.0 | 1.0 |

TABLE 2-continued

Summary of biological components in the bitter blocker*

|  | Run 1 | Run 2 | Average |
|---|---|---|---|
| Fat (acid hydrolysis) | 2.3 | 1.6 | 2.0 |
| Ash | 4.2 | 4.2 | 4.2 |
| Carbohydrates | 86.5 | 87.2 | 86.9 |
| Kilocalories (/100 g) | 371 | 367 | 369 |

*Values reported as percentages of gross powder mass, except for calories as noted.

The lipid content of the bitter blocker is likely responsible for some fraction of its hydrophobic nature. The bitter blocker solubilizes faster when heated to 140-160° F. in aqueous solution. At room temperature the batch took 15 minutes for 0.3 g to solubilize in 500 mL with intermittent agitation. The lipid content, shown in Table 3, is composed of 10 different molecules and interestingly enough contains both essential fatty acids. The molecular structures of these molecules, and all molecules in subsequent tables, are shown in the appendix. The sum of the averages indicates that these data account for 99.3% of the total lipid profile.

TABLE 3

Summary of lipid and fatty acid content in the bitter blocker*

|  | Run 1 | Run 2 | Average |
|---|---|---|---|
| Capric acid | ND | 0.86 | N/A |
| Lauric acid | 6.31 | 8.35 | 7.33 |
| Myristic acid | 4.62 | 5.24 | 4.93 |
| Palmitic acid | 15.9 | 16.3 | 16.1 |
| Stearic acid | 3.59 | 4.48 | 4.04 |
| Oleic acid | 42.4 | 43.2 | 42.8 |
| Linoleic acid | 21.1 | 15.1 | 18.1 |
| α-Linolenic acid | 3.95 | 4.48 | 4.04 |

TABLE 3-continued

Summary of lipid and fatty acid content in the bitter blocker*

|  | Run 1 | Run 2 | Average |
|---|---|---|---|
| Arachidonic acid | 0.74 | 0.86 | 0.80 |
| 11-Eicosenoic acid | 0.63 | 0.82 | 0.73 |

*Values are reported as percentages of the total lipid profile, which is shown to be 2% of the total material on average.
*ND means not detectable. The variation in lipid content reveals inhomogeneity of lipid distribution within the sample.

The fat content, shown in Table 4, provides the breakdown of saturated, poly- and monounsaturated fat, and the omega acid breakdown of the sample.

TABLE 4

Summary of fat content in the bitter blocker*

|  | Run 1 | Run 2 | Average |
|---|---|---|---|
| Saturated fat | 31.1 | 36.1 | 33.6 |
| Polyunsaturated fat | 25.0 | 19.2 | 22.1 |
| Monounsaturated fat | 43.9 | 44.7 | 44.3 |
| Trans fatty acids | ND | ND | N/A |
| Omega 3 fatty acids | 3.95 | 4.08 | 4.02 |
| Omega 6 fatty acids | 21.1 | 15.1 | 18.1 |
| Omega 9 fatty acids | 42.4 | 43.2 | 42.8 |

*Values reported as percentages of total fat content, which was shown to be 2% of the total material on average.
*ND means not detectable. Variation in fat content is reflected in variation of lipid content.

Table 5, shown below, details the salt, some elemental, small molecule and vitamin breakdown of the bitter blocker.

TABLE 5

Summary of salt, key elements, vitamins and small molecules in the bitter blocker*

|  | Run 1 | Run 2 | Average |
|---|---|---|---|
| Salt | 1.05 | 1.04 | 1.05 |
| Calcium | 6520 | 6690 | 6605 |
| Potassium | 3260 | 3380 | 3320 |
| Sodium | 5050 | 5290 | 5170 |
| Iron | 93.4 | 99.2 | 96.3 |
| Magnesium | 1620 | 1600 | 1610 |
| Zinc | 15.7 | 14.0 | 14.9 |
| Copper | 32.8 | 32.8 | 32.8 |
| Selenium | 0.16 | 0.15 | 0.16 |
| Manganese | 3.43 | 3.57 | 3.50 |
| γ-Tocotrienol | 12.75 | 12.67 | 12.71 |
| Ergosterol | 0.34 | 0.45 | 0.40 |
| D-Mannitol | 79.64 | 79.53 | N/A |
| Ascorbic acid | 286.86 | 294.80 | 290.83 |

*Values reported in ppm, except for salt which is a percentage of the total material, and γ-tocotrienol, ergosterol and ascorbic acid, which are reported in µg/g.
*The variation in these data reveals homogeneity in some material, though not in all.

The sparse amino acid content of the bitter blocker, shown in Table 6, is composed of aspartic acid, glutamic acid, cysteine and lysine.

TABLE 6

Summary of amino acids in the bitter blocker*

|  | Run 1 | Run 2 | Average |
|---|---|---|---|
| Aspartic acid | 0.07 | ND | 0.1 |
| Glutamic acid | 0.09 | 0.10 | 0.1 |
| Cystine | 0.01 | ND | N/A |
| Lysine | 0.03 | 0.03 | 0.03 |

*Values reported as percentages of the total material.

Table 7 shows the carbohydrate content and breakdown of the bitter blocker. The β-glucan and chitin are good indicators of total fungal biomass (as is ergosterol and D-mannitol, shown in Table 5). These data account for approximately 99.8% of the carbohydrate profile.

TABLE 7

Summary of saccharide content in the bitter blocker*

|  | Run 1 | Run 2 | Average |
|---|---|---|---|
| Carbohydrates | 86.5 | 87.2 | 86.9 |
| Total Polysaccharides | 487.67 | 449.99 | 468.83 |
| Starch | 59.0 | 58.3 | 58.7 |
| Cellulose | 69.28 | 63.19 | 66.24 |
| Chitin | 114.94 | 127.16 | 121.05 |
| β-glucan | 14.3 | 14.7 | 14.5 |
| Glucuronic acid | 108.08 | 108.07** | 108.07 |
| Xylose | 9.31 | 13.87 | 11.59 |
| Arabinose | 109.02 | 82.63 | 95.83 |
| Mannose + Glucose | 1188.00 | 1165.73 | 1176.86 |
| Sucrose | 1200.88 | 1739.11 | 1469.99 |
| Maltose** | 5900 | N/A | 5900 |

*Carbohydrates and starch reported as percentage of total material, total polysaccharides reported as mg dextran/g, cellulose reported as mg/g, all other values reported as µg/g.
**Maltose assay was only run in singular.

Table 8, shown below, outlines the NBST content of the bitter blocker. The data indicate that salvage pathways are activated to produce the requisite NBST material for growth. Notice how the bitter blocker NBST content is a stripped down set of the *C. sinensis* powder NBST content. The un-retained NBSTs must be intracellular.

TABLE 8

NBST content of Growth Media Powder, Penn State 859 *C. sinensis* submerged culture solids and *C. sinesis* submerged supernatant solids*

|  | GMP | Uridine | AMP | Inosine | Guanosine | Adenosine | Cordycepin | Cytidine | Cytosine | Uracil | Thymine | Adenine | Guanine |
|---|---|---|---|---|---|---|---|---|---|---|---|---|---|
| Media Powder | — | — | — | 2.58 | — | — | — | — | 9.23 | — | — | — | — |
| *C. sinensis* powder | 2.71 | — | 2.17 | — | 1.19 | — | — | 1.55 | 9.32 | 7.97 | 9.56 | 17.52 | — |
| Bitter blocker | 4.02 | — | 2.79 | — | — | — | — | — | — | 13.92 | 23.59 | 85.32 | — |

*Units in µg/g.

A GC/MS investigation revealed three volatile biomolecules present in the bitter blocker. These are hexadecanoic acid methyl ester, 9-octadecanoic acid methyl ester and methyl stearate. Their concentrations will be determined once standards are run.

Example 14

The *C. sinensis* supernatant powder (bitter blocker) is produced by the methods outlined in Example 4 and used with food products on a ppm basis.

TABLE 9

Bitter Blocker Concentration in Various Final Bitter Blocking Product Applications*

| | Recommended Bitter Blocker Concentration (ppm) |
|---|---|
| Steviol Glycoside Mixture | 0.40-1.20 |
| Acesulfame-K | 0.3-1 |
| Aspartame | 0.3-1 |
| Chocolate | 35,000-37,000 |
| Tea | 1,066-1,866 |
| Red Ginseng | 180-220 |
| Zeviva Cola | 0.4-2.0 |
| Coffee Grinds | 7,800-73,000 |
| Coffee Brew | 100-500 |
| 100% Cranberry Juice | 50-3,200 |
| Coconut Water | 100-500 |
| Merlot | 600-3,800 |
| Tequila | 6,400-25,600 |
| Potassium Chloride | 40-60 |
| Vodka | 100-300 |
| Quinoa | 20-30 |
| Amaranth | 40-60 |

*Table 9 does not show how the bitter blocker is formulated into some of these products before application.

Example 15

The *C. sinensis* supernatant powder (bitter blocker, also known as the flavor modulator, also known as ClearTaste) is produced by the methods outlined in Example 4 and used with food products on a ppm basis. An experiment was conducted to test whether or not the flavor modulator at concentrations of 1, 5, 50 and 100 ppm could inhibit the metallic taste of KCl at concentrations of 67, 134 and 201 mM in 20 mL RO water at room temperature (equivalent to 0.5, 1.0 and 1.5% KCl). 1 g of the flavor modulator was dissolved into 0.1 L of RO water in a 100 mL volumetric flask to make a 1% solution three times. Three separate 100 mL volumetric flasks were filled with 0.5, 1.0 and 1.5 g of KCl, and each filled with 0.1 L of the 1% flavor modulator to make 67, 134 and 201 mM KCl solutions with 1% of the flavor modulator. 15 small dixie cups were divided into three groups of 5. Each group successively had 0.1, 0.2 and 0.3 g KCl placed in every cup (for the appropriate %/mM in 20 mL). All cups were filled with 20 mL RO water. One cup in each group was kept as a control. The other cups had 20, 100, 1,000 and 2,000 µL removed one cup in each group by a clean pipette, thereupon having each volume replaced by the same amount of the 1% flavor modulator solution at the appropriate KCl concentration. Each sample was tasted by two tasters. The experiment was recreated and a summary of the results are shown in Table 10. The experiment showed that at appropriate concentrations the flavor modulator can inhibit the metallic taste of KCl, the formulated solution having a purely salty taste with no metallic flavor at all.

TABLE 10

Metallic Taste Modulating Effect of ClearTaste on Room Temperature Potassium Chloride*

| | ClearTaste (ppm) | | | | |
|---|---|---|---|---|---|
| KCl (mM) | 0 | 1 | 5 | 50 | 100 |
| 67 | M NS | M NS | M NS | NM NS | NM NS |
| 134 | M NS | M NS | M NS | NM S | M S |
| 201 | M S | M S | M S | NM S | M S |

*$n_{tasters} = 2$
M = Metallic taste,
NM = No metallic taste,
S = salt taste,
NS = no salt taste Example 16

A 6:1 *quinoa* flour to basic bread flour was made where 25 ppm of the bitter blocker was added as a dry ingredient during kneading. The dough was baked in a Cuisinart CBK-100 series automatic bread-maker on the gluten free setting. A control dough without the bitter blocker was made under the same circumstances. It was concluded in multiple taste tests between 8 different people that the flavor of the treated bread was much less bitter and without the characteristic *quinoa* aftertaste. A similar experiment was conducted with a 1:1 amaranth flour to whole wheat flour mix where the bitter blocker was added at 50 ppm. The same results were observed by the same tasters.

Example 17

A *C. sinensis* culture that had been cultured for 2.5 days at 25° C. in a bioreactor was vacuumed through a 25 µm filter. The filtrate was pasteurized, concentrated and spray dried. The resulting powder was added to a vitamins and mineral nutraceutical mix at 100 ppm. The resulting vitamin/mineral nutraceutical mix was noticeably less bitter and metallic to tasters. The powder derived from the culture filtrate was also used successfully to suppress the bitterness of OTC cough syrups when added up to 1,000 ppm.

The description of the various embodiments has been presented for purposes of illustration and description, but is not intended to be exhaustive or limiting of the invention to the form disclosed. The scope of the present invention is limited only by the scope of the following claims. Many modifications and variations will be apparent to those of ordinary skill in the art. The embodiments described and shown in the FIGURES were chosen and described in order to explain the principles of the invention, the practical application, and to enable others of ordinary skill in the art to understand the invention for various embodiments with various modifications as are suited to the particular use contemplated. All references cited herein are incorporated in their entirety by reference.

What is claimed is:

1. A composition comprising a combination of a food product and a mycelium-free portion from a mycelial liquid tissue culture, wherein the combination comprises a non-nutritive sweetener, wherein the mycelium-free portion is a separated extracellular portion of a liquid tissue culture of *Cordyceps sinensis*, wherein the combination has reduced bitter tastes compared to the food product alone.

2. The composition of claim 1, wherein the mycelium-free portion from the mycelial liquid tissue culture is a dried supernatant.

3. The composition of claim 1, wherein the separated extracellular portion of a liquid tissue culture of *C. sinensis* is obtained by filtration or centrifugation.

4. The composition of claim 1, wherein the mycelium-free portion of the mycelial liquid tissue culture is prepared by a method comprising:
   culturing a mycelial liquid tissue culture in a media;
   separating the supernatant fluid from the mycelial cells; and
   collecting the supernatant fluid of the mycelial liquid tissue culture as the mycelium-free portion.

5. The composition of claim 1, wherein the mycelium-free portion from the mycelial liquid tissue culture is pasteurized or sterilized.

6. The composition of claim 1, wherein the mycelium-free portion from the mycelial liquid tissue culture is collected by filtration or centrifugation.

7. The composition of claim 4, wherein the mycelial liquid tissue culture is centrifuged to separate it from mycelial cells.

8. The composition of claim 4, wherein the culturing step is performed for between one day and sixty days.

9. The composition of claim 1, wherein the non-nutritive sweetener is selected from the group consisting of mogroside, mogroside mixtures, aspartame, acesulfame-k, sucralose, steviol glycoside mixtures, stevia plant parts, and combinations thereof.

\* \* \* \* \*